United States Patent [19]
Tsien et al.

[11] Patent Number: 6,150,176
[45] Date of Patent: Nov. 21, 2000

[54] FLUORESCENT PROTEIN SENSORS FOR MEASURING THE PH OF A BIOLOGICAL SAMPLE

[75] Inventors: Roger Y. Tsien; Juan Llopis, both of La Jolla, Calif.; Rebekka M. Wachter, Creswell; S. James Remington, Eugene, both of Oreg.

[73] Assignees: The Regents of the University of California, Oakland, Calif.; The State of Oregon acting by and through the State of Board of Higher Education on behalf of the Unviersity of Oregon, Eugene, Oreg.

[21] Appl. No.: 09/172,063

[22] Filed: Oct. 13, 1998

Related U.S. Application Data

[63] Continuation-in-part of application No. 09/094,359, Jun. 9, 1998.

[51] Int. Cl.[7] .......................... G01N 33/52; C07K 14/435
[52] U.S. Cl. ................................. 436/86; 530/350
[58] Field of Search ............................... 435/69.7, 257.3, 435/320.1; 530/350; 436/86

[56] References Cited

PUBLICATIONS

Llopis et al. (Jun. 9, 1998) Proc. Natl. Acad. Sci. USA, vol. 95, pp. 6803–6808.
Kneen et al. (Mar. 1998) Biophysical J., vol. 74, pp. 1591–1599 (abstract).
Guttenplan et al. (1973) BBA, vol. 322, pp. 294–300 (abstract).0
Brejc et al. (1997) Proc. Natl. Acad. Sci. USA, vol. 94, pp. 2306–2311.

*Primary Examiner*—Elizabeth Slobodyansky
*Attorney, Agent, or Firm*—Gray Cary Ware & Freidenrich LLP; Lisa A. Haile

[57] ABSTRACT

Disclosed are fluorescent protein sensors for measuring the pH of a sample, nucleic acids encoding them, and methods of use. The preferred fluorescent protein sensors are variants of the green fluorescent protein (GFP) from *Aequorea victoria*. Also disclosed are compositions and methods for measuring the pH of a specific region of a cell, such as the mitochondrial matrix or the Golgi lumen.

38 Claims, 5 Drawing Sheets

FLUORESCENT PROTEIN SENSORS FOR MEASURING THE PH OF A BIOLOGICAL SAMPLE

This application is a continuation-in-part of currently pending U.S. Ser. No. 09/094,359 (herein incorporated by reference), which was filed Jun. 9, 1998.

STATEMENT AS TO FEDERALLY SPONSORED RESEARCH

This invention was made with Government support under Grant No. NS27177, awarded by the National Institutes of Health. The Government has certain rights in this invention.

FIELD OF THE INVENTION

The invention relates generally to compositions and methods for measuring the pH of a sample and more particularly to fluorescent protein sensors for measuring the pH of a biological sample.

BACKGROUND OF THE INVENTION

The pH within various cellular compartments is regulated to provide for the optimal activity of many cellular processes. In the secretory pathway, posttranslational processing of secretory proteins, the cleavage of prohormones, and the retrieval of escaped luminal endoplasmic reticulum proteins are all pH-dependent.

Several techniques have been described for measuring intracellular pH. Commonly used synthetic pH indicators can be localized to the cytosol and nucleus, but not selectively in organelles other than those in the endocytotic pathway. In addition, some cells are resistant to loading with cell-permeant dyes because of physical barriers such as the cell wall in bacteria, yeast, and plants, or the thickness of a tissue preparation such as brain slices.

Several methods have been described for measuring pH in specific regions of the cell. One technique uses microinjection of fluorescent indicators enclosed in liposomes. Once inside the cell, the liposomes fuse with vesicles in the trans-Golgi, and the pH of the intracellular compartments is determined by observing the fluorescence of the indicator. This procedure can be laborious, and the fluorescence of the indicator can be diminished due to leakage of the fluorescent indicator from the Golgi, or flux of the fluorescent indicator out of the Golgi as part of the secretory traffic in the Golgi pathway. In addition, the fusion of the liposomes and components of the Golgi must take place at 37° C.; however, this temperature facilitates leakage and flux of the fluorescent indicator from the Golgi.

A second method for measuring pH utilizes retrograde transport of fluorescein-labeled verotoxin 1B, which stains the entire Golgi complex en route to the endoplasmic reticulum. This method can be used, however, only in cells bearing the receptor globotriaosyl ceramide on the plasma membrane, and it may be limited by the residence time of the verotoxin in transit through the Golgi.

In a third method, intracellular pH has been measured using the chimeric protein CD25-TGN38, which cycles between the trans-Golgi network and the plasma membrane. At the plasma membrane, the CD25-motif binds extracellular anti-CD25 antibodies conjugated with a pH-sensitive fluorophore. Measurement of fluorescence upon return of the bound complex to the Golgi can be used to measure the pH of the organelle.

SUMMARY OF THE INVENTION

The invention is based on the discovery that proteins derived from the *Aequorea victoria* green fluorescence protein (GFP) show reversible changes in fluorescence over physiological pH ranges.

Accordingly, in one aspect, the invention provides a method for determining the pH of a sample by contacting the sample with an indicator including a first fluorescent protein moiety whose emission intensity changes as the pH varies between 5 and 10, exciting the indicator, and the determining the intensity at a first wavelength. The emission intensity of the first fluorescent protein moiety indicates the pH of the sample.

In another aspect, the invention provides a method for determining the pH of a region of a cell by introducing into the cell a polynucleotide encoding a polypeptide including a first fluorescent protein moiety whose emission intensity changes as the pH varies between 5 and 10, culturing the cell under conditions that permit expression of the polynucleotide, and determining the intensity at a first wavelength. The emission intensity of the first fluorescent protein moiety indicates the pH of the sample.

In a further aspect, the invention provides a functional engineered fluorescent protein whose amino acid sequence is substantially identical to the amino acid sequence of the 238 amino acid *Aequorea victoria* green fluorescence protein shown in FIG. 3 of U.S. Ser. No. 08/911,825 (SEQ ID NO:2), and whose emission intensity changes as pH varies between 5 and 10.

In another aspect, the invention provides a polynucleotide encoding the functional engineered fluorescent protein.

The invention also includes a kit useful for the detection of pH in a sample, e.g., a region of a cell. The kit includes a carrier means containing one or more containers comprising a first container containing a polynucleotide encoding a polypeptide including a first fluorescent protein moiety whose emission intensity changes as the pH varies between 5 and 10.

BRIEF DESCRIPTION OF THE DRAWINGS

FIG. 3A is a graph showing single wavelength fluorescence intensities of GT-EYFP and GT-ECFP in the Golgi region of a HeLa cell. FIG. 3B is a graph showing the ratio of GT-EYFP/GT-ECFP fluorescence in the same cell as a function of time.

DETAILED DESCRIPTION

Figure 1:
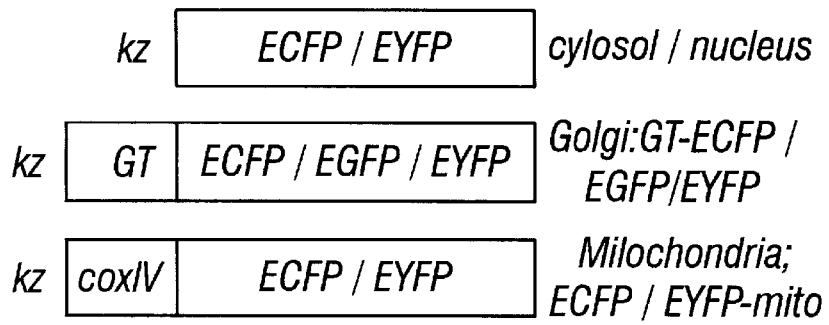
FIG. 1 is a schematic diagram depicting fluorescent protein sensors used as indicators of intracellular pH.

The invention provides genes encoding fluorescent sensor proteins, or fragments thereof, whose fluorescence is sensitive to changes in pH at a range between 5 and 10. The proteins of the invention are useful for measuring the pH of a sample. The sample can be a biological sample and can include an intracellular region of a cell, such as the lumen of the mitochondria or golgi. The pH of a sample is determined by observing the fluorescence of the fluorescent sensor protein.

The fluorescent protein pH sensor have a broad applicability to cells and organisms that are amenable to gene transfer. Problems associated with the use of other agents used to measure pH, e.g., problems associated with permeabilizing cells to ester-containing agents, leakage of agents, or hydrolysis of agents are avoided. With the fluorescent protein pH sensors of the invention, no leakage occurs over the course of a typical measurement, even when the measurement is made at 37° C.

Compositions and methods described herein also avoid the need to express and purify large quantities of soluble recombinant protein, purify and label it in vitro, microinject it back into cells. An important advantage of the fluorescent protein pH sensors of the invention is that they can be delivered to cells in the form of polynucleotides encoding the protein sensor fused to a targeting signal or signals. The targeting signal directs the expression of the protein sensors to restricted cell locations. Thus, it is possible to measure the pH of a precisely defined cellular region or organelle.

Polynucleotides and Polypeptides

In a first aspect, the invention provides a functional engineered fluorescent protein whose amino acid sequence is substantially identical to the 238 amino acid *Aequorea victoria* green fluorescence protein shown in FIG. 3 of U.S. Ser. No. 08/911,825 (SEQ ID NO:2). The term "fluorescent protein" refers to any protein capable of emitting light when excited with appropriate electromagnetic radiation, and which has an amino acid sequence that is either natural or engineered and is derived from the amino acid sequence of Aequorea-related fluorescent protein. The term "fluorescent protein pH sensor" refers to a fluorescent protein whose emitted light varies with changes in pH from 5 to 10.

The invention also includes functional polypeptide fragments of a fluorescent protein pH sensor. As used herein, the term "functional polypeptide fragment" refers to a polypeptide which possesses biological function or activity which is identified through a defined functional assay and which is associated with a particular biologic, morphologic, or phenotypic alteration in the cell. The term "functional fragments of a functional engineered fluorescent protein" refers to fragments of a functional engineered protein that retain a function of the engineered fluorescent protein, e.g., the ability to fluoresce in a pH-dependent manner over the pH range 5 to 10. Biologically functional fragments can vary in size from a polypeptide fragment as small as an epitope to a large polypeptide.

Minor modifications of the functional engineered fluorescent protein may result in proteins which have substantially equivalent activity as compared to the unmodified counterpart polypeptide as described herein. Such modifications may be deliberate, as by site-directed mutagenesis, or may be spontaneous. All of the polypeptides produced by these modifications are included herein as long as the pH-dependent fluorescence of the engineered protein still exists.

A functional engineered fluorescent protein includes amino acid sequences substantially the same as the sequence set forth in SEQ ID NO:2, and whose emission intensity changes as pH varies between 5 and 10. In some embodiments the emission intensity of the functional engineered fluorescent protein changes as pH varies between 5 and 8.5.

By "substantially identical" is meant a protein or polypeptide that retains the activity of a functional engineered protein, or nucleic acid encoding the same, and which exhibits at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 85%, more preferably 90%, more preferably 95%, more preferably 98%, and most preferably 99% identical at the amino acid level to one of the sequences of EGFP (SEQ ID NO:3), EYFP (SEQ ID NO:4), ECFP (SEQ ID NO:6), EYFP-V68L/Q69K (SEQ ID NO:5), YFP H148G (SEQ ID NO:7), or YFP H148Q (SEQ ID NO:8).

Homology is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

In some embodiments, the amino acid sequence of the protein includes one of the following sets of substitutions in the amino acid sequence of the Aequorea green fluorescent protein (SEQ ID NO:2): F64L/S65T/H231L, referred to herein as EGFP (SEQ ID NO:3); S65G/S72A/T203Y/H231L, referred to herein as EYFP (SEQ ID NO:4); S65G/V68L/Q69K/S72A/T203Y/H231L, referred to herein as EYFP-V68L/Q69K (SEQ ID NO:5); K26R/F64L/S65T/Y66W/N146I/M153T/V163A/N164H/H231L, referred to herein as ECFP (SEQ ID NO:6). The amino acid sequences of EGFP, EYFP, ECFP, and EYFP-V68L/Q69K are shown in Tables 1–4, respectively. The amino acids are numbered with the amino acid following the initiating methionine assigned the '1' position. Thus, F64L corresponds to a substitution of leucine for phenylalanine in the 64th amino acid following the initiating methionine.

TABLE 1

EGFP Amino Acid Sequence (SEQ ID NO:3)
MVSKGEELFTGVVPILVELDGDVNGHKFSVSGEGEGDATYGKLTLKFICTT

GKLPVPWPTLVTTLTYGVQCFSRYPDHMKQHDFFKSAMPEGYVQERTIFFK

DDGNYKTRAEVKFEGDTLVNRIELKGIDFKEDGNILGHKLEYNYNSHNVYI

MADKQKNGIKVNFKIRHNIEDGSVQLADHYQQNTPIGDGPVLLPDNHYLST

QSALSKDPNEKRDHMVLLEFVTAAGITLGMDELYK

TABLE 2

EYFP Amino Acid Sequence (SEQ ID NO:4)
MVSKGEELFTGVVPILVELDGDVNGHKFSVSGEGEGDATYGKLTLKFICTT

GKLPVPWPTLVTTFGYGVQCFARYPDHMKQHDFFKSAMPEGYVQERTIFFK

DDGNYKTRAEVKFEGDTLVNRIELKGIDFKEDGNILGHKLEYNYNSHNVYI

MADKQKNGIKVNFKIRHNIEDGSVQLADHYQQNTPIGDGPVLLPDNHYLSY

QSALSKDPNEKRDHMVLLEFVTAAGITLGMDELYK

TABLE 3

EYFP-V68L/Q69K Amino Acid Sequence (SEQ ID NO:5)
MVSKGEELFTGVVPILVELDGDVNGH-
KFSVSGEGEGDATYGKLTLKFICTT

GKLPVPWPTLVTTFGYGLKCFARYPDH-
MKQHDFFKSAMPEGYVQERTIFFK

DDGNYKTRAEVKFEGDTLVNRIELKGID-
FKEDGNILGHKLEYNYNSHNVYI

MADKQKNGIKVNFKIRHNIEDGS-
VQLADHYQQNTPIGDGPVLLPDNHYLSY

QSALSKDPNEKRDHMVLLEFVTAAGITLGMDELYK

TABLE 4

ECFP Amino Acid Sequence (SEQ ID NO:6)
MVSKGEELFTGVVPILVELDGDVNGHRFSVSGEGEGDATYGKLTLKFICTT

GKLPVPWPTLVTTLTWGVQCFSRYPDHMKQHDFFKSAMPEGYVQERTIFFK

DDGNYKTRAEVKFEGDTLVNRIELKGIDFKEDGNILGHKLEYNYISHNVYI

TADKQKNGIKAHFKIRHNIEDGSVQLADHYQQNTPIGDGPVLLPDNHYLST

QSALSKDPNEKRDHMVLLEFVTAAGITLGMDELYK

In other embodiments, the amino acid sequence of the protein is based on the sequence of the wild-type Aequorea green fluorescent protein, but includes the substitution H148G (SEQ ID NOs:7 and 9) or H148Q (SEQ ID NOs:8 and 10). In specific embodiments, these substitutions can be present along with other substitutions, e.g., the proteins can include the substitutions S65G/V68L/S72A/Q80R/H148G/T203Y, which is referred to herein as the YFP H148G mutant (SEQ ID NO: 7); S65G/V68L/S72A/Q80R/H148Q/T203Y, which is referred to herein as the YFP H148Q mutant (SEQ ID NO: 8); as well as S65G/S72A/H148G/T203Y/H231L, which is referred to herein as EYFP-H148G (SEQ ID NO: 9); and S65G/S72A/H148Q/T203Y/H231L, which is referred to herein as EYFP-H148Q (SEQ ID NO: 10). The amino acid sequences of these mutants are shown in Tables 5–8, respectively.

TABLE 5

Amino Acid Sequence of YFP H148G (SEQ ID NO:7)
MSKGEELFTGVVPILVELDGDVNGHKFSVSGEGEGDATYGKLTLKFICTTG

KLPVPWPTLVTTFGYGLQCFARYPDHMKRHDFFKSAMPEGYVQERTIFFKD

DGNYKTRAEVKFEGDTLVNRIELKGIDFKEDGNILGHKLEYNYNSGNVYIM

ADKQKNGIKVNFKIRHNIEDGSVQLADHYQQNTPIGDGPVLLPDNHYLSYQ

SALSKDPNEKRDHMVLLEFVTAAGITHGMDELYKtz,1/32

TABLE 6

EGFP Amino Acid Sequence of YFP H148Q (SEQ ID NO:8)
MSKGEELFTGVVPILVELDGDVNGHKFSVSGEGEGDATYGKLTLKFICTTG

KLPVPWPTLVTTFGYGLQCFARYPDHMKRHDFFKSAMPEGYVQERTIFFKD

DGNYKTRAEVKFEGDTLVNRIELKGIDFKEDGNILGHKLEYNYNSQNVYIM

ADKQKNGIKVNFKIRHNIEDGSVQLADHYQQNTPIGDGPVLLPDNHYLSYQ

SALSKDPNEKRDHMVLLEFVTAAGITHGMDELYK

TABLE 7

EGFP Amino Acid Sequence of EYFP-H148G (SEQ ID NO:9)
MVSKGEELFTGVVPILVELDGDVNGHKFSVSGEGEGDATYGKLTLKFICTT

GKLPVPWPTLVTTFGYGVQCFARYPDHMKQHDFFKSAMPEGYVQERTIFFK

DDGNYKTRAEVKFEGDTLVNRIELKGIDFKEDGNILGHKLEYNYNSGNVYI

MADKQKNGIKVNFKIRHNIEDGSVQLADHYQQNTPIGDGPVLLPDNHYLSY

QSALSKDPNEKRDHMVLLEFVTAAGITLGMDELYK

TABLE 8

Amino Acid Sequence of EYFP-H148Q (SEQ ID NO:10)
MVSKGEELFTGVVPILVELDGDVNGHKFSVSGEGEGDATYGKLTLKFICTT

GKLPVPWPTLVTTFGYGVQCFARYPDHMKQHDFFKSAMPEGYVQERTIFFK

TABLE 8-continued

Amino Acid Sequence of EYFP-H148Q

DDGNYKTRAEVKFEGDTLVNRIELKGIDFKEDGNILGHKLEYNYNSQNVYI

MADKQKNGIKVNFKIRHNIEDGSVQLADHYQQNTPIGDPVLLPDNHYLSY

QSALSKDPNEKRDHMVLLEFVTAAGITLGMDELYK

In some embodiments, the protein or polypeptide is substantially purified. By "substantially pure protein or polypeptide" is meant a functional engineered fluorescent polypeptide which has been separated from components which naturally accompany it. Typically, the protein or polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, of the protein. A substantially pure protein may be obtained, for example, by extraction from a natural source (e.g., a plant cell); by expression of a recombinant nucleic acid encoding a functional engineered fluorescent protein; or by chemically synthesizing the protein. Purity can be measured by any appropriate method, e.g., those described in column chromatography, polyacrylamide gel electrophoresis, or by HPLC analysis.

A protein or polypeptide is substantially free of naturally associated components when it is separated from those contaminants which accompany it in its natural state. Thus, a protein or polypeptide which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

The invention also provides polynucleotides encoding the functional engineered fluorescent protein described herein. These polynucleotides include DNA, cDNA, and RNA sequences which encode functional engineered fluorescent proteins. It is understood that all polynucleotides encoding functional engineered fluorescent proteins are also included herein, as long as they encode a protein or polypeptide whose fluorescent emission intensity changes as pH varies between 5 and 10. Such polynucleotides include naturally occurring, synthetic, and intentionally manipulated polynucleotides. For example, the polynucleotide may be subjected to site-directed mutagenesis. The polynucleotides of the invention include sequences that are degenerate as a result of the genetic code. Therefore, all degenerate nucleotide sequences are included in the invention as long as the amino acid sequence of the functional engineered fluorescent protein or derivative is functionally unchanged.

Specifically disclosed herein is a polynucleotide sequence encoding a functional engineered fluorescent protein that includes one of the following sets of substitutions in the amino acid sequence of the Aequorea green fluorescent protein (SEQ ID NO:2): S65G/S72A/T203Y/H231L, S65G/V68L/Q69K/S72A/T203Y/H231L, or K26R/F64L/S65T/Y66W/N1461I/M153T/V163A/N164H/H231L. In specific embodiments, the DNA sequences encoding EGFP, EYFP, ECFP, EYFP-V68L/Q69K, YFP H148G, YFP H148Q, EYFP-H148G, and EYFP-H148Q are those shown in Tables 9–16 (SEQ ID NOs: 11 to 18), respectively.

The nucleic acid encoding functional engineered fluorescent proteins may be reflect the codon choice in the native *A. victoria* coding sequence, or, alternatively, may be chosen to reflect the optimal codon frequencies used in the organism in which the proteins will be expressed. Thus, nucleic acids encoding a target functional engineered protein to be expressed in a human cell may have use a codon choice that is optimized for mammals, or especially humans.

TABLE 9

EGFP Nucleic Acid Sequence (SEQ ID NO:11)
ATGGTGAGCAAGGGCGAGGAGCTGTTCACCGGGGTGGTGCCCATCCTGGTC

GAGCTGGACGGCGACGTAAACGGCCACAAGTTCAGCGTGTCCGGCGAGGGC

GAGGGCGATGCCACCTACGGCAAGCTGACCCTGAAGTTCATCTGCACCACC

GGCAAGCTGCCCGTGCCCTGGCCCACCCTCGTGACCACCCTGACCTACGGC

GTGCAGTGCTTCAGCCGCTACCCCGACCACATGAAGCAGCACGACTTCTTC

AAGTCCGCCATGCCCGAAGGCTACGTCCAGGAGCGCACCATCTTCTTCAAG

GACGACGGCAACTACAAGACCCGCGCCGAGGTGAAGTTCGAGGGCGACACC

CTGGTGAACCGCATCGAGCTGAAGGGCATCGACTTCAAGGAGGACGGCAAC

ATCCTGGGGCACAAGCTGGAGTACAACTACAACAGCCACAACGTCTATATC

ATGGCCGACAAGCAGAAGAACGGCATCAAGGTGAACTTCAAGATCCGCCAC

AACATCGAGGACGGCAGCGTGCAGCTCGCCGACCACTACCAGCAGAACACC

CCCATCGGCGACGGCCCCGTGCTGCTGCCCGACAACCACTACCTGAGCACC

CAGTCCGCCCTGAGCAAAGACCCCAACGAGAAGCGCGATCACATGGTCCTG

CTGGAGTTCGTGACCGCCGCCGGGATCACTCTCGGCATGGACGAGCTGTAC

AAGTAA

TABLE 10

EYFP Nucleic Acid Sequence (SEQ ID NO:12)
ATGGTGAGCAAGGGCGAGGAGCTGTTCACCGGGGTGGTGCCCATCCTGGTC

GAGCTGGACGGCGACGTAAACGGCCACAAGTTCAGCGTGTCCGGCGAGGGC

GAGGGCGATGCCACCTACGGCAAGCTGACCCTGAAGTTCATCTGCACCACC

GGCAAGCTGCCCGTGCCCTGGCCCACCCTCGTGACCACCTTCGGCTACGGC

GTGCAGTGCTTCGCCCGCTACCCCGACCACATGAAGCAGCACGACTTCTTC

AAGTCCGCCATGCCCGAAGGCTACGTCCAGGAGCGCACCATCTTCTTCAAG

GACGACGGCAACTACAAGACCCGCGCCGAGGTGAAGTTCGAGGGCGACACC

CTGGTGAACCGCATCGAGCTGAAGGGCATCGACTTCAAGGAGGACGGCAAC

ATCCTGGGGCACAAGCTGGAGTACAACTACAACAGCCACAACGTCTATATC

ATGGCCGACAAGCAGAAGAACGGCATCAAGGTGAACTTCAAGATCCGCCAC

AACATCGAGGACGGCAGCGTGCAGCTCGCCGACCACTACCAGCAGAACACC

CCCATCGGCGACGGCCCCGTGCTGCTGCCCGACAACCACTACCTGAGCTAC

CAGTCCGCCCTGAGCAAAGACCCCAACGAGAAGCGCGATCACATGGTCCTG

CTGGAGTTCGTGACCGCCGCCGGGATCACTCTCGGCATGGACGAGCTGTAC

AAGTAA

TABLE 11

ECFP Nucleic Acid Sequence (SEQ ID NO:13)
ATGGTGAGCAAGGGCGAGGAGCTGTTCACCGGGGTGGTGCCCATCCTGGTC

GAGCTGGACGGCGACGTAAACGGCCACAGGTTCAGCGTGTCCGGCGAGGGC

GAGGGCGATGCCACCTACGGCAAGCTGACCCTGAAGTTCATCTGCACCACC

GGCAAGCTGCCCGTGCCCTGGCCCACCCTCGTGACCACCCTGACCTGGGGC

GTGCAGTGCTTCGAGCGCTACCCCGACCACATGAAGCAGCACGACTTCTT

CAAGTCCGCCATGCCCGAAGGCTACGTCCAGGAGCGTACCATCTTCTTCAA

GGACGACGGCAACTACAAGACCCGCGCCGAGGTGAAGTTCGAGGGCGACAC

CCTGGTGAACCGCATCGAGCTGAAGGGCATCGACTTCAAGGAGGACGGCAA

CATCCTGGGGCACAAGCTGGAGTACAACTACATCAGCCACAACGTCTATAT

CACCGCCGACAAGCAGAAGAACGGCATCAAGGCCCACTTCAAGATCCGCCA

CAACATCGAGGACGGCAGCGTGCAGCTCGCCGACCACTACCAGCAGAACAC

CCCCATCGGCGACGGCCCCGTGCTGCTGCCCGACAACCACTACCTGAGCAC

CCAGTCCGCCCTGAGCAAAGACCCCAACGAGAAGCGCGATCACATGGTCCT

GCTGGAGTTCGTGACCGCCGCCGGGATCACTCTCGGCATGGACGAGCTGTA

CAAGTAA

TABLE 12

EYFP-V68L/Q69K Nucleic Acid Sequence (SEQ ID NO:14)
ATGGTGAGCAAGGGCGAGGAGCTGTTCACCGGGGTGGTGCCCATCCTGGTC

GAGCTGGACGGCGACGTAAACGGCCACAAGTTCAGCGTGTCCGGCGAGGGC

GAGGGCGATGCCACCTACGGCAAGCTGACCCTGAAGTTCATCTGCACCACC

GGCAAGCTGCCCGTGCCCTGGCCCACCCTCGTGACCACCTTCGGCTACGGC

CTGAAGTGCTTCGCCCGCTACCCCGACCACATGAAGCAGCACGACTTCTTC

AAGTCCGCCATGCCCGAAGGCTACGTCCAGGAGCGCACCATCTTCTTCAAG

GACGACGGCAACTACAAGACCCGCGCCGAGGTGAAGTTCGAGGGCGACACC

CTGGTGAACCGCATCGAGCTGAAGGGCATCGACTTCAAGGAGGACGGCAAC

ATCCTGGGGCACAAGCTGGAGTACAACTACAACAGCCACAACGTCTATATC

ATGGCCGACAAGCAGAAGAACGGCATCAAGGTGAACTTCAAGATCCGCCAC

AACATCGAGGACGGCAGCGTGCAGCTCGCCGACCACTACCAGCAGAACACC

CCCATCGGCGACGGCCCCGTGCTGCTGCCCGACAACCACTACCTGAGCTAC

CAGTCCGCCCTGAGCAAAGACCCCAACGAGAAGCGCGATCACATGGTCCTG

CTGGAGTTCGTGACCGCCGCCGGGATCACTCTCGGCATGGACGAGCTGTAC

AAGTAA

TABLE 13

Nucleotide Sequence of the YFP H148G Coding Region (SEQ ID NO:15)
ATGAGTAAAGGAGAAGAACTTTTCACTGGAGTTGTCCCAATTCTTGTTGAA

TTAGATGGTGATGTTAATGGGCACAAATTTTCTGTCAGTGGAGAGGGTGAA

GGTGATGCAACATACGGAAAACTTACCCTTAAATTTATTTGCACTACTGGA

AAACTACCTGTTCCATGGCCAACACTTGTCACTACTTTCGGTTATGGTCTT

CAATGCTTTGCAAGATACCCAGATCATATGAAACGGCATGACTTTTTCAAG

AGTGCCATGCCCGAAGGTTATGTTCAGGAAAGAACTATATTTTTCAAAGAT

GACGGGAACTACAAGACACGTGCTGAAGTCAAGTTTGAAGGTGATACCCTT

GTTAATAGAATCGAGTTAAAAGGTATTGATTTTAAAGAAGATGGAAACATT

CTTGGACACAAATTGGAATACAACTATAACTCAGGCAATGTATACATCATG

GCAGACAAACAAAAGAATGGAATCAAAGTTAACTTCAAAATTAGACACAAC

ATTGAAGATGGAAGCGTTCAACTAGCAGACCATTATCAACAAAATACTCCA

ATTGGCGATGGCCCTGTCCTTTTACCAGACAACCATTACCTGTCCTATCAA

TCTGCCCTTTCGAAAGATCCCAACGAAAGAGAGACCACATGGTCCTTCTT

GAGTTTGTAACAGCTGCTGGGATTACACATGGCATGGATGAACTATAAAA

TABLE 14

Nucleotide Sequence of the YFP H148Q Coding Region (SEQ ID NO:16)
ATGAGTAAAGGAGAAGAACTTTTCACTGGAGTTGTCCCAATTCTTGTTGAA

TTAGATGGTGATGTTAATGGGCACAAATTTTCTGTCAGTGGAGAGGGTGAA

GGTGATGCAACATACGGAAAACTTACCCTTAAATTTATTTGCACTACTGGA

AAACTACCTGTTCCATGGCCAACACTTGTCACTACTTTCGGTTATGGTCTT

CAATGCTTTGCAAGATACCCAGATCATATGAAACGGCATGACTTTTTCAAG

AGTGCCATGCCCGAAGGTTATGTTCAGGAAAGAACTATATTTTTCAAAGAT

GACGGGAACTACAAGACACGTGCTGAAGTCAAGTTTGAAGGTGATACCCTT

GTTAATAGAATCGAGTTAAAAGGTATTGATTTTAAAGAAGATGGAAACATT

CTTGGACACAAATTGGAATACAACTATAACTCAGGCAATGTATACATCATG

GCAGACAAACAAAAGAATGGAATCAAAGTTAACTTCAAAATTAGACACAAC

ATTGAAGATGGAAGCGTTCAACTAGCAGACCATTATCAACAAAATACTCCA

ATTGGCGATGGCCCTGTCCTTTTACCAGACAACCATTACCTGTCCTATCAA

TCTGCCCTTTCGAAAGATCCCAACGAAAGAGAGACCACATGGTCCTTCTT

GAGTTTGTAACAGCTGCTGGGATTACACATGGCATGGATGAACTATACAAA

TABLE 15

Nucleotide Sequence of the EYFP-H148G Coding Region (SEQ ID NO:17)
ATGGTGAGCAAGGGCGAGGAGCTGTTCACCGGGGTGGTGCCCATCCTGGTC

GAGCTGGACGGCGACGTAAACGGCCACAAGTTCAGCGTGTCCGGCGAGGGCG

TABLE 15-continued

Nucleotide Sequence of the EYFP-H148G Coding Region

AGGGCGATGCCACCTACGGCAAGCTGACCCTGAAGTTCATCTGCACCCCGG

CAAGCTGCCCGTGCCCTGGCCCACCCTCGTGACCACCTTCGGCTACGGCGT

GCAGTGCTTCGCCCGCTACCCGACCACATGAAGCAGCACGACTTCTTCAAG

TCCGCCATGCCCGAAGGCTACGTCCAGGAGCGCACCATCTTCTTCAAGGAC

GACGGCAACTACAAGACCCGCGCCGAGGTGAAGTTCGAGGGCGACACCCTG

GTGAACCGCATCGAGTGAAGGGCATCGACTTCAAGGAGGACGGCAACATCC

TGGGGCACAAGCTGGAGTACAACTACAACAGCGGCAACTCTATATCATGGC

CGACAAGCAGAAGAACGGCATCAAGGTGAACTTCAAGATCCGCCACAACAT

CGAGGACGGCAGCGTGCAGCTCGCCGACCACTACCAGCAGAACACCCCCAT

CGGCGACGGCCCCGTGCTGCTGCCCGACAACCACTACCTGAGCTACCAGTC

CGCCCTGAGCAAAGACCCCAACGAGAAGCGCGATCACATGGTCCTGCTGGA

GTTCGTGCCGCCGCCGGGATCACTCTCGGCATGGACGAGCTGTACAAGTAA

TABLE 16

Nucleotide Sequence of the EYFP-H148Q Coding Region (SEQ ID NO:18)
ATGGTGAGCAAGGGCGAGGAGCTGTTCACCGGGGTGGTGCCCATCCTGGTC

GAGCTGGACGGCGACGTAAACGGCCACCAGTTCAGCGTGTCCGGCGAGGGC

GAGGGCGATGCCACCTACGGCAAGCTGACCCTGAAGTTCATCTGCACCACC

GGCAAGCTGCCCGTGCCCTGGCCCACCCTCGTGACCACCTTCGGCTACGGC

GTGCAGTGCTTCGCCCGCTACCCCGACCACATGAAGCAGCACGACTTCTTC

AAGTCCGCCATGCCCGAAGGCTACGTCCAGGAGCGCACCATCTTCTTCAAG

GACGACGGCAACTACAAGACCCGCGCCGAGGTGAAGTTCGAGGGCGACACC

CTGGTGAACCGCATCGAGCTGAAGGGCATCGACTTCAAGGAGGACGGCAAC

ATCCTGGGGCACAAGCTGGAGTACAACTACAACAGCCAGAACGTCTATATC

ATGGCCGACAAGCAGAAGAACGGCATCAAGGTGAACTTCAAGATCCGCCAC

AACATCGAGGACGGCAGCGTGCAGCTCGCCGACCACTACCAGCAGAACACC

CCCATCGGCGACGGCCCCGTGCTGCTGCCCGACAACCACTACCTGAGCTAC

CAGTCCGCCCTGAGCAAAGACCCCAACGAGAAGCGCGATCACATGGTCCTG

CTGGAGTTCGTGACCGCCGCCGGGATCACTCTCGGCATGGACGAGCTGTAC

AAGTAA

The term "polynucleotide" refers to a polymeric form of nucleotides of at least 10 bases in length. The nucleotides can be ribonucleotides, deoxyribonucleotides, or modified forms of either type of nucleotide. The term includes single and double stranded forms of DNA. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

A "substantially identical" nucleic acid sequence codes for a substantially identical amino acid sequence as defined above.

The functional engineered fluorescent protein can also include a targeting sequence to direct the fluorescent protein to particular cellular sites by fusion to appropriate organellar targeting signals or localized host proteins. A polynucleotide encoding a targeting sequence can be ligated to the 5' terminus of a polynucleotide encoding the fluorescence such that the targeting peptide is located at the amino terminal end of the resulting fusion polynucleotide/polypeptide. The targeting sequence can be, e.g., a signal peptide. In the case of eukaryotes, the signal peptide is believed to function to transport the fusion polypeptide across the endoplasmic reticulum. The secretory protein is then transported through the Golgi apparatus, into secretory vesicles and into the extracellular space or, preferably, the external environment. Signal peptides which can be utilized according to the invention include pre-pro peptides which contain a proteolytic enzyme recognition site. Other signal peptides with similar properties to pro-calcitonin described herein are known to those skilled in the art, or can be readily ascertained without undue experimentation.

The targeting sequence can also be a nuclear localization sequence, an endoplasmic reticulum localization sequence, a peroxisome localization sequence, a mitochondrial localization sequence, or a localized protein. Targeting sequences can be targeting sequences which are described, for example, in "Protein Targeting", chapter 35 of Stryer, L., Biochemistry (4th ed.). W. H. Freeman, 1995. The localization sequence can also be a localized protein. Some important targeting sequences include those targeting the nucleus (KKKRK) (SEQ ID NO:35), mitochondrion (the 12 amino terminal amino acids of the cytochrome c oxidase subunit IV gene, or the amino terminal sequence MLRTSSLFTR-RVQPSLFRNILRLQST (SEQ ID NO:36), endoplasmic reticulum (KDEL (SEQ ID NO:37) at the C-terminus, assuming a signal sequence present at N-terminus), peroxisome (SKF at C-terminus), prenylation or insertion into plasma membrane (CaaX, CC, CXC, or CCXX at C-terminus), cytoplasmic side of plasma membrane (fusion to SNAP-25), or the Golgi apparatus (fusion to the amino terminal 81 amino acids of human type II membrane-anchored protein galactosyltransferase, or fusion to furin).

Examples of targeting sequences linked to functional engineered fluorescent proteins include GT-EYFP (SEQ ID NO:22), GT-ECFP, GT-EGFP (SEQ ID NO:21), and GT-EYFP-V68L/Q69K, which are targeted to the Golgi apparatus using sequences from the GT protein; and mito-ECFP (SEQ ID NO: 19) and mito-EYFP (SEQ ID NO:20), which are targeted to the mitochondrial matrix using sequences from the amino terminal region of the cytochrome c oxidase subunit IV gene. The EYFP, ECFP, EGFP, and EYFP-V68L/Q69K amino acid sequences, as well as nucleic acids encoding these polypeptides, are described above. The GT-derived targeting sequence corresponds to the 81 amino terminal amino acids of the human GT sequence. The GT amino acid sequences, and the polynucleotide sequences encoding the GT amino acid sequences, are described in Genbank Accession No. M70427 and Mengle-Gaw et al., Biochem. Biophys. Res. Commun. 176 (3), 1269–1276 (1991).

Amino acid sequences of mito-ECFP, mito-EYFP, GT-EGFP, GT-EYFP, mito-YFP H148G, mito-YFP H148Q, mito-EYFP H148G, mito-EYFP-H148Q are shown in Tables 17–24.

In specific embodiments, nucleic acid sequences encoding targeting sequences linked to functional engineered fluorescent proteins have the sequences shown in Tables 25–32.

TABLE 17 mito-ECFP Amino Acid Sequence (SEQ ID NO:19)
MLSLRQSIRFFKRSGIMVSKGEELFTGVVPILVELDGDVNGHRFSVSGEGE
GDATYGKLTLKFICTTGKLPVPWPTLVTTLTWGVQCFSRYPDHMKQHDFFK
SAMPEGYVQERTIFFKDDGNYKTRAEVKFEGDTLVNRIELKGIDFKEDGNI
LGHKLEYNYISHNVYITADKQKNGIKAHFKIRHNIEDGSVQLADHYQQNTP
IGDGPVLLPDNHYLSTQSALSKDPNEKRDHMVLLEFVTAAGITLGMDELYK

TABLE 18 mito-EYFP Amino Acid Sequence (SEQ ID NO:20)
MLSLRQSIRFFKRSGIMVSKGEELFTGVVPILVELDGDVNGHKFSVSGEGE
GDATYGKLTLKFICTTGKLPVPWPTLVTTFGYGVQCFARYPDHMKQHDFFK
SAMPEGYVQERTIFFKDDGNYKTRAEVKFEGDTLVNRIELKGIDFKEDGNI
LGHKLEYNYNSHNVYIMADKQKNGIKVNFKIRHNIEDGSVQLADHYQQNTP
IGDGPVLLPDNHYLSYQSALSKDPNEKRDHMVLLEFVTAAGITLGMDELYK

TABLE 19

GT-EGFP Amino Acid Sequence (SEQ ID NO:21)
MRLREPLLSGAAMPGASLQRACRLLVAVCALHLGVTLVYYLAGRDLSRLPQ
LVGVSTPLQGGSNSAAAIGQSSGELRTGGAMDPMVSKGEELFTGVVPILVE
LDGDVNGHKFSVSGEGEGDATYGKLTLKFICTTGKLPVPWPTLVTTLTYGV
QCFSRTPDHMKQHDFFKSAMPEGYVQERTIFFKDDGNYKTRAEVKFEGDTL
VNRIELKGIDFKEDGNILGHKLEYNYNSHNVYIMADKQKNGIKVNFKIRHN
IEDGSVQLADHYQQNTPIGDGPVLLPDNHYLSTQSALSKDPNEKRDHMVLL
EFVTAAGITLGMDELYK

TABLE 20

GT-EYFP Amino Acid Sequence (SEQ ID NO:22)
t1,1 MRLREPLLSGAAMPGASLQRACRLLVAV-
CALHLGVTLVYYLAGRDLSRLPQ
LVGVSTPLQGGSNSAAAIGQSSGELRTGGAMDPMVSKGEELFTGVVPILVE
LDGDVNGHKFSVSGEGEGDATYGKLTLKFICTTGKLPVPWPTLVTTFGYGV
QCFARYPDHMKQHDFFKSAMPEGYVQERTIFFKDDGNYKTRAEVKFEGDTL
VNRIELKGIDFKEDGNILGHKLEYNYNSHNVYIMADKQKNGIKVNFKIRHN
IEDGSVQLADHYQQNTPIGDGPVLLPDNHYLSYQSALSKDPNEKRDHMVLL
EFVTAAGITLGMDELYK*

TABLE 21 mito-YFP-H148G Amino Acid Sequence (SEQ ID NO:23)
MLRTSSLFTRRVQPSLFRNILRLQSTSKGEELFTGVVPILVELDGDVNGHK
FSVSGEGEGDATYGKLTLKFICTTGKLPVPWPTLVTTFGYGLQCFARYPDH
MKRHDFFKSAMPEGYVQERTIFFKDDGNYKTRAEVKFEGDTLVNRIELKGI
DFKEDGNILGHKLEYNYNSGNVYIMADKQKNGIKVNFKIRHNIEDGSVQLA
DHYQQNTPIGDGPVLLPDNHYLSYQSALSKDPNEKRDHMVLLEFVTAAGIT
HGMDELYK

TABLE 22 mito-YFP-H148Q Amino Acid Sequence (SEQ ID NO:24)
MLRTSSLFTRRVQPSLFRNILRLQSTSKGEELFTGVVPILVELDGDVNGHK
FSVSGEGEGDATYGKLTLKFICTTGKLPVPWPTLVTTFGYGLQCFARYPDH
MKRHDFFKSAMPEGYVQERTIFFKDDGNYKTRAEVKFEGDTLVNRIELKGI
DFKEDGNILGHKLEYNYSQNVYIMADKQKNGIKVNFKIRHNIEDGSVQLA
DHYQQNTPIGDGPVLLPDNHYLSYQSALSKDPNEKRDHMVLLEFVTAAGIT
HGMDELYK

TABLE 23 mito-EYFP-H148G Amino Acid Sequence (SEQ ID NO:25)
MLRTSSLFTRRVQPSLFRNILRLQSTMVSKGEELFTGVVPILVELDGDVNG
HKFSVSGEGEGDATYGKLTLKFICTTGKLPVPWPTLVTTFGYGVQCFARYP
DHMKQHDFFKSAMPEGYVQERTIFFKDDGNYKTRAEVKFEGDTLVNRIELK
GIDFKEDGNILGHKLEYNYNSGNVYIMADKQKNGIKVNFKIRHNIEDGSVQ
LADHYQQNTPIGDGPVLLPDNHYLSYQSALSKDPNEKRDHMVLLERVTAAG
ITLGMDELYK

TABLE 24 mito-EYFP-H148Q Amino Acid Sequence (SEQ ID NO:26)
MLRTSSLFTRRVQPSLFRNILRLQSTMVSKGEELFTGVVPILVELDGDVNG
HKFSVSGEGEGDATYGKLTLKFICTTGKLPVPWPTLVTTFGYGVQCFARYP
DHMKQHDFFKSAMPEGYVQERTIFFKDDGNYKTRAEVKFEGDTLVNRIELK
GIDFKEDGNILGHKLEYNYSQNVYIMADKQKNGIKVNFKIRHNIEDGSVQ
LADHYQQNTPIGDGPVLLPDNHYLSYQSALSKDPNEKRDHMVLLEFVTAAG
ITLGMDELYK

TABLE 25

GT-ECFP Nucleic Acid Sequence (SEQ ID NO:27)
ATGAGGCTTCGGGAGCCGCTCCTGAGCGGCGCCGCGATGCCAGGCGCGTCC
CTACAGCGGGCCTGCCGCCTGCTCGTGGCCGTCTGCGCTCTGCACCTTGGC
GTCACCCTCGTTTACTACCTGGCTGGCCGCGACCTGAGCCGCCTGCCCCAA
CTGGTCGGAGTCTCCACACCGCTGCAGGGCGGCTCGAACAGTGCCGCCGCC
ATCGGGCAGTCCTCCGGGGAGCTCCGGACCGGAGGGGCCATGGATCCCATG
GTGAGCAAGGGCGAGGAGCTGTTCACCGGGGTGGTGCCCATCCTGGTCGAG
CTGGACGGCGACGTAAACGGCCACAGGTTCAGCGTGTCCGGCGAGGGCGAG
GGCGATGCCACCTACGGCAAGCTGACCCTGAAGTTCATCTGCACCACCGGC
AAGCTGCCCGTGCCCTGGCCCACCCTCGTGACCACCCTGACCTGGGGCGTG
CAGTGCTTCAGCCGCTACCCCGACCACATGAAGCAGCACGACTTCTTCAAG
TCCGCCATGCCCGAAGGCTACGTCCAGGAGCGTACCATCTTCTTCAAGGAC
GACGGCAACTACAAGACCCGCGCCGAGGTGAAGTTCGAGGGCGACACCCTG
GTGAACCGCATCGAGCTGAAGGGCATCGACTTCAAGGAGGACGGCAACATC
CTGGGGCACAAGCTCCAGTACAACTACATCAGCCACAACGTCTATATCACC
GCCGACAAGCAGAAGAACGGCATCAAGGCCCACTTCAAGATCCGCCACAAC
ATCGAGGACGGCAGCGTGCAGCTCGCCGACCACTACCAGCAGAACACCCCC
ATCGGCGACGGCCCCGTGCTGCTGCCCGACAACCACTACCTGAGCACCCAG
TCCGCCCTGAGCAAAGACCCCAACGAGAAGCGCGATCACATGGTCCTGCTG
GAGTTCGTGACCGCCGCCGGACCACTCTCGGCATGGACGAGCTGTACAAGT
AA

TABLE 26 mito-EYFP Nucleic Acid Sequence (SEQ ID NO:28)
ATGCTGAGCCTGCGCCAGAGCATCCGCTTCTTCAAGCGCAGCGGCATCATG
GTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAG
GGCGATGCCACCTACGGCAAGCTGACCCTGAAGTTCATCTGCACCACCGGC
TGCCCGTGCCCTGGCCCACCCTCGTGACCACCTTCGGCTACGGCGTGCAGT
GCTTCGCCCGCTACCCCGACCACATGAAGCAGCACGACTTCTTCAAGTCCG
CCATGCCCGAAGGCTACGTCCAGGAGCGCACCATCTTCTTCAAGGACGACG
GCAACTACAAGACCCGCGCCGAGGTGAAGTTCGAGGGCGACACCCTGGTGA
ACCGCATCGAGCTGAAGGGCATCGACTTCAAGGAGGACGGCAACATCCTGG
GGCACAAGCTGGAGTACAACTACAACAGCCACAACGTCTATATCATGGCCG
ACAAGCAGAAGAACGGCATCAAGGTGAACTTCAAGATCCGCCACAACATCG
AGGACGGCAGCGTGCAGCTCGCCGACCACTACCAGCAGAACACCCCCATCG
GCGACGGCCCCGTGCTGCTGCCCGACAACCACTACCTGAGCTACCAGTCCG

TABLE 26-continued mito-EYFP Nucleic Acid Sequence

CCCTGAGCAAAGACCCCAACGAGAAGCGCGATCACATGGTCCTGCTGGAGT
TCGTGACCGCCGCCGGGATCACTCTCGGCATGGACGAGCTGTACAAGTAA

TABLE 27

GT-RGFP Nucleic Acid Sequence (SEQ ID NO:29)
ATGAGGCTTCGGGAGCCGCTCCTGAGCGGCGCCGCGATGCCAGGCGCGTCC
CTACAGCGGGCCTGCCGCCTGCTCGTGGCCGTCTGCGCTCTGCACCTTGGC
GTCACCCTCGTTTACTACCTGGCTGGCCGCGACCTGAGCCGCCTGCCCCAA
CTGGTCGGAGTCTCCACACCGCTGCAGGGCGGCTCGAACAGTGCCGCCGCC
ATCGGGCAGTCCTCCGGGGAGCTCCGGACCGGAGGGGCCATGGATCCCATG
GTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAG
GGCGATGCCACCTACGGCAAGCTGACCCTGAAGTTCATCTGCACCACCGGC
AAGCTGCCCGTGCCCTGGCCCACCCTCGTGACCACCCTGACCTACGGCGTG
CAGTGCTTCAGCCGCTACCCCGACCACATGAAGCAGCACGACTTCTTCAAG
TCCGCCATGCCCGAAGGCTACGTCCAGGAGCGCACCATCTTCTTCAAGGAC
GACGGCAACTACAAGACCCGCGCCGAGGTGAAGTTCGAGGGCGACACCCTG
GTGAACCGCATCGAGCTGAAGGGCATCGACTTCAAGGAGGACGGCAACATC
CTGGGGCACAAGCTGGAGTACAACTACAACAGCCACAACGTCTATATCATG
GCCGACAAGCAGAAGAACGGCATCAAGGTGAACTTCAAGATCCGCCACAAC
ATCGAGGACGGCAGCGTGCAGCTCGCCGACCACTACCAGCAGAACACCCCC
ATCGGCGACGGCCCCGTGCTGCTGCCCGACAACCACTACCTGAGCACCCAG
TCCGCCCTGAGCAAAGACCCCAACGAGAAGCGCGATCACATGGTCCTGCTG
GAGTTCGTGACCGCCGCCGGGATCACTCTCGGCATGGACGAGCTGTACAAG
TAA

TABLE 28

GT-EYFP Nucleic Acid Sequence (SEQ ID NO:30)
ATGAGGCTTCGGGAGCCGCTCCTGAGCGGCGCCGCGATGCCAGGCGCGTCC
CTACAGCGGGCCTGCCGCCTGCTCGTGGCCGTCTGCGCTCTGCACCTTGGC
GTCACCCTCGTTTACTACCTGGCTGGCCGCGACCTGAGCCGCCTGCCCCAA
CTGGTCGGAGTCTCCACACCGCTGCAGGGCGGCTCGAACAGTGCCGCCGCC
ATCGGGCAGTCCTCCGGGGAGCTCCGGACCGGAGGGGCCATGGATCCCATG
GTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAG
GGCGATGCCACCTACGGCAAGCTGACCCTGAAGTTCATCTGCACCACCGGC
AAGCTGCCCGTGCCCTGGCCCACCCTCGTGACCACCTTCGGCTACGGCGTG
CAGTGCTTCGCCCGCTACCCCGACCACATGAAGCAGCACGACTTCTTCAAGT

TABLE 28-continued

GT-EYFP Nucleic Acid Sequence

CCGCCATGCCCGAAGGCTACGTCCAGGAGCGCACCATCTTCTTCAAGGACG

ACGGCAACTACAAGACCCGCGCCGAGGTGAAGTTCGAGGGCGACACCCTGG

TGAACCGCATCGAGCTGAAGGGCATCGACTTCAAGGAGGACGGCAACATCC

TGGGGCACAAGCTGGAGTACAACTACAACAGCCACAACGTCTATATCATGG

CCGACAAGCAGAAGAACGGCATCAAGGTGAACTTCAAGATCCGCCACAACA

TCGAGGACGGCAGCGTGCAGCTCGCCGACCACTACCAGCAGAACACCCCCA

TCGGCGACGGCCCCGTGCTGCTGCCCGACAACCACTACCTGAGCTACCAGT

CCGCCCTGAGCAAAGACCCCAACGAGAAGCGCGATCACATGGTCCTGCTGG

AGTTCGTGACCGCCGCCGGGATCACTCTCGGCATGGACGAGCTGTACAAGT

AA

TABLE 29 mito-YFP H148G Nucleic Acid Sequence (SEQ ID NO:31)
ATGCTGAGCCTGCGCCAGAGCATCCGCTTCTTCAAGCGCAGCGGCATCATG

AGTAAAGGAGAAGAACTTTTCACTGGAGTTGTCCCAATTCTTGTTGAATTA

GATGGTGATGTTAATGGGCACAAATTTTCTGTCAGTGGAGAGGGTGAAGGT

GATGCAACATACGGAAAACTTACCCTTAAATTTATTTGCACTACTGGAAAA

CTACCTGTTCCATGGCCAACACTTGTCACTACTTTCGGTTATGGTCTTCAA

TGCTTTGCAAGATACCCAGATCATATGAAACGGCATGACTTTTTCAAGAGT

GCCATGCCCGAAGGTTATGTTCAGGAAAGAACTATATTTTTCAAAGATGAC

GGGAACTACAAGACACGTGCTGAAGTCAAGTTTGAAGGTGATACCCTTGTT

AATAGAATCAGATTAAAAGGTATTGATTTTAAAGAAGATGGAAACATTCTT

GGACACAAATTGGAATACAACTATAACTCAGGCAATGTATACATCATGGCA

GACAAACAAAAGAATGGAATCAAAGTTAACTTCAAAATTAGACACAACATT

GAAGATGGAAGCGTTCAACTAGCAGACCATTATCAACAAAATACTCCAATT

GGCGATGGCCCTGTCCTTTTACCAGACAACCATTACCTGTCCTATCAATCT

GCCCTTTCGAAAGATCCCAACGAAAAGAGAGACCACATGGTCCTTCTTGAG

TTTGTAACAGCTGCTGGGATTACACATGGCATGGATGAACTATACAAA

TABLE 30 mito-YFP H148Q Nucleic Acid Sequence (SEQ ID NO:32)
ATGCTGAGCCTGCGCCAGAGCATCCGCTTCTTCAAGCGCAGCGGCATCATG

AGTAAAGGAGAAGAACTTTTCACTGGAGTTGTCCCAATTCTTGTTGAATTA

GATGGTGATGTTAATGGGCACAAATTTTCTGTCAGTGGAGAGGGTGAAGGT

GATGCAACATACGGAAAACTTACCCTTAAATTTATTTGCACTACTGGAAAA

CTACCTGTTCCATGGCCAACACTTGTCACTACTTTCGGTTATGGTCTTCAA

TGCTTTGCAAGATACCCAGATCATATGAAACGGCATGACTTTTTCAAGAGT

TABLE 30-continued mito-YFP H148Q Nucleic Acid Sequence

GCCATGCCCGAAGGTTATGTTCAGGAAAGAACTATATTTTTCAAAGATGAC

GGGAACTACAAGACACGTGCTGAAGTCAAGTTTGAAGGTGATACCCTTGTT

AATAGAATCAGATTAAAAGGTATTGATTTTAAAGAAGATGGAAACATTCTT

GGACACAAATTGGAATACAACTATAACTCAGGCAATGTATACATCATGGCA

GACAAACAAAAGAATGGAATCAAAGTTAACTTCAAAATTAGACACAACATT

GAAGATGGAAGCGTTCAACTAGCAGACCATTATCAACAAAATACTCCAATT

GGCGATGGCCCTGTCCTTTTACCAGACAACCATTACCTGTCCTATCAATCT

GCCCTTTCGAAAGATCCCAACGAAAAGAGAGACCACATGGTCCTTCTTGAG

TTTGTAACAGCTGCTGGGATTACACATGGCATGGATGAACTATACAAA

TABLE 31 mito-EYFP-H148G Nucleic Acid Sequence
(SEQ ID NO:33)

ATGCTGAGCCTGCGCCAGAGCATCCGCTTCTTCAAGCGCAGCGGCATCATG

GTGAGCAAGGGCGAGGAGCTGTTCACCGGGGTGGTGCCCATCCTGGTCGAG

CTGGACGGCGACGTAAACGGCCACAAGTTCAGCGTGTCCGGCGAGGGCGAG

GGCGATGCCACCTACGGCAAGCTGACCCTGAAGTTCATCTGCACCACCGGC

AAGCTGCCCGTGCCCTGGCCCACCCTCGTGACCACCTTCGGCTACGGCGTG

CAGTGCTTCGCCCGCTACCCCGACCACATGAAGCAGCACGACTTCTTCAAG

TCCGCCATGCCCGAAGGCTACGTCCAGGAGCGCACCATCTTCTTCAAGGAC

GACGGCAACTACAAGACCCGCGCCGAGGTGAAGTTCGAGGGCGACACCCTG

GTGAACCGCATCGAGCTGAAGGGCATCGACTTCAAGGAGGACGGCAACATC

CTGGGGCACAAGCTGGAGTACAACTACAACAGCGGCAACGTCTATATCATG

GCCGACAAGCAGAAGAACGGCATCAAGGTGAACTTCAAGATCCGCCACAAC

ATCGAGGACGGCAGCGTGCAGCTCGCCGACCACTACCAGCAGAACACCCCC

ATCGGCGACGGCCCCGTGCTGCTGCCCGACAACCACTACCTGAGCTACCAG

TCCGCCCTGAGCAAAGACCCCAACGAGAAGCGCGATCACATGGTCCTGCTG

GAGTTCGTGACCGCCGCCGGGATCACTCTCGGCATGGACGAGCTGTACAAG

TAA

TABLE 32 mito-EYFP-H148Q Nucleic Acid Sequence
(SEQ ID NO:34)

ATGCTGAGCCTGCGCCAGAGCATCCGCTTCTTCAAGCGCAGCGGCATCATG

GTGAGCAAGGGCGAGGAGCTGTTCACCGGGGTGGTGCCCATCCTGGTCGAG

CTGGACGGCGACGTAAACGGCCACAAGTTCAGCGTGTCCGGCGAGGGCGAG

GGCGATGCCACCTACGGCAAGCTGACCCTGAAGTTCATCTGCACCACCGGC

AAGCTGCCCGTGCCCTGGCCCACCCTCGTGACCACCTTCGGCTACGGCGTG

CAGTGCTTCGCCCGCTACCCCGACCACATGAAGCAGCACGACTTCTTCAAG

TABLE 32-continued mito-EYFP-H148Q Nucleic Acid Sequence
(SEQ ID NO:34)

TCCGCCATGCCCGAAGGCTACGTCCAGGAGCGCACCATCTTCTTCAAGGAC

GACGGCAACTACAAGACCCGCGCCGAGGTGAAGTTCGAGGGCGACACCCTG

GTGAACCGCATCGAGCTGAAGGGCATCGACTTCAAGGAGGACGGCAACATC

CTGGGGCACAAGCTGGAGTACAACTACAACAGCCAGAACGTCTATATCATG

GCCGACAAGCAGAAGAACGGCATCAAGGTGAACTTCAAGATCCGCCACAAC

ATCGAGGACGGCAGCGTGCAGCTCGCCGACCACTACCAGCAGAACACCCCC

ATCGGCGACGGCCCCGTGCTGCTGCCCGACAACCACTACCTGAGCTACCAG

TCCGCCCTGAGCAAAGACCCCAACGAGAAGCGCGATCACATGGTCCTGCTG

GAGTTCGTGACCGCCGCCGGGATCACTCTCGGCATGGACGAGCTGTACAAG

TAA

The fluorescent indicators can be produced as proteins fused to other fluorescent indicators or targeting sequences by recombinant DNA technology. Recombinant production of fluorescent proteins involves expressing nucleic acids having sequences that encode the proteins. Nucleic acids encoding fluorescent proteins can be obtained by methods known in the art. For example, a nucleic acid encoding the protein can be isolated by polymerase chain reaction of cDNA from A. victoria using primers based on the DNA sequence of A. victoria green fluorescent protein. PCR methods are described in, for example, U.S. Pat. No. 4,683, 195; Mullis, et al. Cold Spring Harbor Symp. Quant. Biol. 51:263 (1987), and Erlich, ed., PCR Technology, (Stockton Press, NY, 1989). Mutant versions of fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations. See, e.g., U.S. patent application Ser. No. 08/337,915, filed Nov. 10, 1994 or International application PCT/US95/14692, filed Nov. 10, 1995.

The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used herein, "operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components whose presence can influence expression, and can also include additional components whose presence is advantageous, for example, leader sequences and fusion partner sequences.

As used herein, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989). Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982).

Techniques for the isolation and purification of polypeptides of the invention expressed in prokaryotes or eukaryotes may be by any conventional means such as, for example, preparative chromatographic separations and immunological separations such as those involving the use of monoclonal or polyclonal antibodies or antigen.

A variety of host-expression vector systems may be utilized to express fluorescent indicator coding sequence. These include but are not limited to microorganisms such as bacteria transformed with recombinant bacteriophage DNA, plasmid DNA or cosmid DNA expression vectors containing a fluorescent indicator coding sequence; yeast transformed with recombinant yeast expression vectors containing the fluorescent indicator coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a fluorescent indicator coding sequence; insect cell systems infected with recombinant virus expression vectors (e.g., baculovirus) containing a fluorescent indicator coding sequence; or animal cell systems infected with recombinant virus expression vectors (e.g., retroviruses, adenovirus, vaccinia virus) containing a fluorescent indicator coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516–544, 1987). For example, when cloning in bacterial systems, inducible promoters such as pL of bacteriophage $\lambda$., plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted fluorescent indicator coding sequence.

In bacterial systems a number of expression vectors may be advantageously selected depending upon the use intended for the fluorescent indicator expressed. For example, when large quantities of the fluorescent indicator are to be produced, vectors which direct the expression of high levels of fusion protein products that are readily purified may be desirable. Those which are engineered to contain a cleavage site to aid in recovering fluorescent indicator are preferred. In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp.516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. DM Glover, IRL Press, Wash., D.C., 1986). Alternatively, vectors may be used which promote integration of foreign DNA sequences into the yeast chromosome.

In cases where plant expression vectors are used, the expression of a fluorescent indicator coding sequence may be driven by any of a number of promoters. For example, viral promoters such as the 35S RNA and 19S RNA promoters of CaMV (Brisson, et al., Nature 310:511–514, 1984), or the coat protein promoter to TMV (Takamatsu, et al., EMBO J. 6:307–311, 1987) may be used; alternatively, plant promoters such as the small subunit of RUBISCO (Coruzzi, et al., 1984, EMBO J. 3:1671–1680; Broglie, et al., Science 224:838–843, 1984); or heat shock promoters, e.g., soybean hsp17.5-E or hsp17.3-B (Gurley, et al., Mol. Cell. Biol. 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421–463, 1988; and Grierson & Corey, Plant Molecular Biology, 2d Ed., Blackie, London, Ch. 7–9, 1988.

An alternative expression system which could be used to express fluorescent indicator is an insect system. In one such system, *Autographa californica* nuclear polyhedrosis virus (AcNPV) is used as a vector to express foreign genes. The virus grows in *Spodoptera frugiperda* cells. The fluorescent indicator coding sequence may be cloned into non-essential regions (for example, the polyhedrin gene) of the virus and placed under control of an AcNPV promoter (for example the polyhedrin promoter). Successful insertion of the fluorescent indicator coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed, see Smith, et al., J. Viol. 46:584, 1983; Smith, U.S. Pat. No. 4,215,051.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and WI38. Primary cell lines, such as neonatal rat myocytes, can also be used.

Mammalian cell systems which utilize recombinant viruses or viral elements to direct expression may be engineered. For example, when using adenovirus expression vectors, the fluorescent indicator coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, Proc. Natl. Acad. Sci. USA, 81: 3655–3659, 1984). Alternatively, the vaccinia virus 7.5K promoter may be used (e.g., see, Mackett, et al., Proc. Natl. Acad. Sci. USA ,79: 7415–7419, 1982; Mackett, et al., J. Virol. 49: 857–864, 1984; Panicali, et al., Proc. Natl. Acad. Sci. USA 79: 4927–4931, 1982). Of particular interest are vectors based on bovine papilloma virus which have the ability to replicate as extrachromosomal elements (Sarver, et al., Mol. Cell. Biol. 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone &

Mulligan, Proc. Natl. Acad. Sci. USA, 81:6349–6353, 1984). High level expression may also be achieved using inducible promoters, including, but not limited to, the metallothionein IIA promoter and heat shock promoters.

The recombinant nucleic acid can be incorporated into an expression vector including expression control sequences operatively linked to the recombinant nucleic acid. The expression vector can be adapted for function in prokaryotes or eukaryotes by inclusion of appropriate promoters, replication sequences, markers, etc.

DNA sequences encoding the fluorescence indicator polypeptide of the invention can be expressed in vitro or in vivo by DNA transfer into a suitable recombinant host cell. As used herein, "recombinant host cells" are cells in which a vector can be propagated and its DNA expressed. The term also includes any progeny of the subject host cell. It is understood that all progeny may not be identical to the parental cell since there may be mutations that occur during replication. However, such progeny are included when the term "recombinant host cell" is used. Methods of stable transfer, in other words when the foreign DNA is continuously maintained in the host, are known in the art.

The expression vector can be transfected into a host cell for expression of the recombinant nucleic acid. Recombinant host cells can be selected for high levels of expression in order to purify the fluorescent indicator fusion protein. *E. coli* is useful for this purpose. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell taken in vivo from a transgenic animal.

Transgenic Animals

In another embodiment, the invention provides a transgenic non-human animal that expresses a polynucleotide sequence which encodes a fluorescent protein pH sensor.

The "non-human animals" of the invention comprise any non-human animal having a polynucleotide sequence which encodes a fluorescent indicator. Such non-human animals include vertebrates such as rodents, non-human primates, sheep, dog, cow, pig, amphibians, and reptiles. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic, i.e., animals which include the exogenous genetic material within all of their cells in both alleles. 50% of the resulting animals will include the exogenous genetic material within one allele and 25% will include no exogenous genetic material.

Retroviral infection can also be used to introduce transgene into a non-human animal. The developing non-human embryo can be cultured in vitro to the blastocyst stage. During this time, the blastomeres can be targets for retro viral infection (Jaenisch, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al., Proc. Natl. Acad. Sci. USA 82:6927–6931, 1985; Van der Putten, et al., Proc. Natl. Acad. Sci USA 82:6148–6152, 1985). Transfection is easily and efficiently obtained by culturing the blastomeres on a monolayer of virus-producing cells (Van der Putten, supra; Stewart, et al., EMBO J. 6:383–388, 1987). Alternatively, infection can be performed at a later stage. Virus or virus-producing cells can be injected into the blastocoele (D. Jahner et al., Nature 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (D. Jahner et al., supra). A third type of target cell for transgene introduction is the embryonal stem cell (ES). ES cells are obtained from pre-implantation embryos cultured in vitro and fused with embryos (M. J. Evans et al. Nature 292:154–156, 1981; M. O. Bradley et al., Nature 309: 255–258,1984; Gossler, et al., Proc. Natl. Acad. Sci USA 83: 9065–9069, 1986; and Robertson et al., Nature 322:445–448, 1986). Transgenes can be efficiently introduced into the ES cells by DNA transfection or by retrovirus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468–1474, 1988).

"Transformed" means a cell into which (or into an ancestor of which) has been introduced, by means of recombinant nucleic acid techniques, a heterologous polynucleotide. "Heterologous" refers to a polynucleotide sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode the fluorescent indicator which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

Detection of pH Using Fluorescent Indicator Proteins

In another embodiment, the invention provides a method for determining the pH of a sample by contacting the sample with an indicator including a first fluorescent protein moiety whose emission intensity changes as pH varies between pH 5 and 10, exciting the indicator, and then determining the intensity of light emitted by the first fluorescent protein moiety at a first wavelength. The emission intensity of the first fluorescent protein moiety indicates the pH of the sample.

The fluorescent protein moiety can be a functional engineered protein substantially identical to the amino acid sequence of Aequorea green fluorescence protein (SEQ ID NO:2). Preferred green fluorescence proteins include those having a functional engineered fluorescent protein that includes one of the following sets of substitutions in the amino acid sequence of the Aequorea green fluorescent protein (SEQ ID NO:2): S65G/S72A/T203Y/H231L, S65G/V68L/Q69K/S72A/T203Y/H231L, or K26R/F64L/S65T/Y66W/N146I/M153T/V163A/N164H/H231L. Other preferred green fluorescence proteins include those having a functional engineered fluorescent protein that includes H148G or H148Q substitutions in the Aequorea green fluorescent protein. These proteins include the YFP H148G (SEQ ID NO:7) and YFP H148Q (SEQ ID NO:8) proteins described above.

The sample in which pH is to be measured can be a biological sample, e.g., a biological tissue such as an extracellular matrix, blood or lymphatic tissue, or a cell. The method is particularly suitable for measuring pH in a specific region of the cell, e.g., the cytosol, or an organellar space such as the inner mitochondrial matrix, the lumen of the Golgi, cytosol, the endoplasmic reticulum, the chloroplast lumen, the lumen of lysosome, or the lumen of an endosome.

In some embodiments, the first fluorescent protein moiety is linked to a targeting sequence that directs the fluorescent protein to a desired cellular compartment. Examples of targeting sequences include the amino terminal 81 amino acids of human type II membrane-anchored protein galactosyltransferase for directing the fluorescent indicator protein to the Golgi and the amino terminal 12 amino acids of the presequence of subunit IV of cytochrome c oxidase for directing a fluorescent pH indicator protein to the mitochondrial matrix. The 12 amino acids of the presequence of subunit IV of cytochrome c oxidase may be linked to the pH fluorescent indicator protein through a linker sequence, e.g., Arg-Ser-Gly-Ile (SEQ ID NO:38).

In another embodiment, the invention provides a method of determining the pH of a region of a cell by introducing into the cell a polynucleotide encoding a polypeptide including an indicator having a first fluorescent protein moiety whose emission intensity changes as pH varies between 5 and 10, culturing the cell under conditions that permit expression of the polynucleotide; exciting the indicator; and determining the intensity of the light emitted by the first protein moiety at a first wavelength. The emission intensity of the first fluorescent protein moiety indicates the pH of the region of the cell in which the indicator is present.

The polynucleotide can be introduced using methods described above. Thus, the method can be used to measure intracellular pH in cells cultured in vitro, e.g., HeLa cells, or alternatively in vivo, e.g., in cells of an animal carrying a transgene encoding a pH-dependent fluorescent indicator protein.

Fluorescence in the sample can be measured using a fluorometer. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. If desired, a multi-axis translation stage can be used to move a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., *Principles of Fluorescence Spectroscopy*, New York:Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N. J., *Modern Molecular Photochemistry*, Menlo Park: Benjamin/Cummings Publishing Col, Inc. (1978), pp. 296–361.

The pH can be analyzed on cells in vivo, or from samples derived from cells transfected with polynucleotides or proteins expressing the pH indicator proteins. Because fluorescent pH indicator proteins can be expressed recombinantly inside a cell, the pH in an intracellular region, e.g., an organelle, or an extracellular region of an organism can be determined simply by determining changes in fluorescence.

Fluorescent protein pH sensors may vary in their respective $pK_a$, and the differences in $pK_a$ can be used to select the most suitable fluorescent protein sensor for a particular application. In general, a sensor protein should be used whose $pK_a$ is close to the pH of the sample to be measured. Preferably the $pK_a$ is within 1.5 pH unit of the sample. More preferably the $pK_a$ is within 1 pH unit, and still more preferably the $pK_a$ is within 0.5 pH unit of the sample.

Thus, a fluorescent protein pH sensor having a pKa of about 7.1, e.g., the EYFP mutant described below, is preferred for determining the pH of cytosolic, Golgi, and mitochondrial matrix pH areas of a cell. The YFP-H148G, YFP-H148Q, EYFP-H148G and EYFP-H148Q mutants are well-suited for measuring the pH of alkaline environments, e.g., mitochondrial matrix, as they have a pKa of 7.5 and 8.0, respectively.

For more acidic organelles, a fluorescence sensor protein having a lower $pK_a$, e.g., a $pK_a$ of about 6.1, is preferred.

To minimize artefactually low fluorescence measurements that occur due to cell movement or focusing, the fluorescence of a fluorescent protein pH sensor can be compared to the fluorescence of a second sensor, e.g., a second fluorescent protein pH sensor, that is also present in the measured sample. The second fluorescent protein pH sensor should have an emission spectra distinct from the first fluorescent protein pH sensor so that the emission spectra of the two sensors can be distinguished. Because experimental conditions such as focusing and cell movement will affect fluorescence of the second sensor as well as the first sensor, comparing the relative fluorescence of the two sensors allows for the normalization of fluorescence.

A convenient method of comparing the samples is to compute the ratio of the fluorescence of the first fluorescent protein pH sensor to that of the second fluorescent protein pH sensor.

Kits

The materials and components described for use in the methods of the invention are ideally suited for the preparation of a kit. Such a kit may comprise a carrier means being compartmentalized to receive one or more container means such as vials, tubes, and the like, each of the container means comprising one of the separate elements to be used in the method. For example, one of the container means may comprise a polynucleotide encoding a fluorescent protein pH sensor. A second container may further comprise fluorescent protein pH sensor. The constituents may be present in liquid or lyophilized form, as desired.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to limit the scope of the invention described in the claims.

EXAMPLES

Example 1

Construction of Fluorescent Protein pH Sensors

Fluorescent protein pH sensors were constructed by engineering site-specific mutations in polynucleotides encoding forms of the *Aequorea victoria* green fluorescent protein (GFP). The starting GFP variant was the polynucleotide encoding the GFP variant EGFP (for enhanced green fluorescent protein). The EGFP variant had the amino acid substitutions F64L/S65T/H231L relative to the wild-type *Aequorea victoria* GFP sequence.

The ECFP (enhanced cyan fluorescent protein) mutant was constructed by altering the EGFP polynucleotide sequence so that it encoded a protein having the amino acid substitutions K26R/F64L/S65T/Y66W/N146I/M153T/V163A/N164H/H231L relative to the wild-type GFP amino acid sequence. A second variant, named EYFP (enhanced yellow fluorescent protein) was constructed by altering the EGFP polynucleotide to encode a protein having the amino acid substitutions S65G/S72A/T203Y/H231L relative to the amino acid sequence of GFP. A third variant, named EYFP/V68L/Q69K, was constructed by altering the EGFP polynucleotide to encode a protein having the amino acid substitutions S65G/V68L/Q69K/S72A/T203Y/H231L relative to the amino acid sequence of GFP.

A HindIII site and Kozak consensus sequence (GCCACCATG) was introduced at the 5' end of the polynucleotide encoding the GFP variants, and an EcoR1 site was added at the 3' end of the gene of each indicator, and the fragments were ultimately ligated into the HindIII/EcoR1 sites of the mammalian expression vector pcDNA3 (Invitrogen). EGFP and EYFP mutant proteins with no targeting signals were used as indicators of pH in the cytosol or nucleus.

To construct fluorescent protein pH sensors to use as pH indicators in the Golgi, polynucleotides encoding the 81 N-terminal amino acids of the type II membrane-anchored protein galactosyltransferase (GT:UDP-galactose-β,1,4-galactosyltransferase. EC 2.4.1.22) ligated to polynucleotides encoding EGFP, ECFP, or EYFP. The polynucleotides encoding the resulting proteins were named GT-EGFP, GT-ECFP, and GT-EYFP, respectively.

Mitochondrial matrix fluorescent protein pH sensors were constructed by attaching polynucleotides encoding 12 amino acids at the amino terminus of the presequence of subunit IV of cytochrome c oxidase (Hurt et al, EMBO J. 4:2061–68 (1985) to a polynucleotide encoding the amino acid sequence Arg-Sea-Gly-Ile (SEQ ID NO:38), which in turn was ligated to polynucleotides encoding ECFP or EYFP. These constructs were labeled ECFP-mito or EYFP-mito.

The constructs used to examine intracellular pH are summarized in FIG. 1.

Example 2 pH Titration of Fluorescent Sensor Proteins in vitro

The pH sensitivity of the fluorescence of the proteins ECFP, EGFP, EYFP, GT-EGFP, and GT-EYFP was first examined.

Absorbance spectra were obtained in a Cary 3E spectrophotometer (Varian). For pH titration, a monochromator-equipped fluorometer (Spex Industries, NJ) and a 96-well microplate fluorometer (Cambridge Technology) were used. In the latter case the filters used for excitation were 482±10 (460±18 for ECFP) and for emission were 532±14. Filters were named as the center wavelength±the half-bandwidth, both in nm. The solutions for cuvette titration contained 125 mM KCl, 20 mM NaCl, 0.5 mM $CaCl_2$, 0.5 mM $MgCl_2$, and 25 mM of one of the following buffers—acetate, Mes, Mops, Hepes, bicine, and Tris.

Figure 2A:
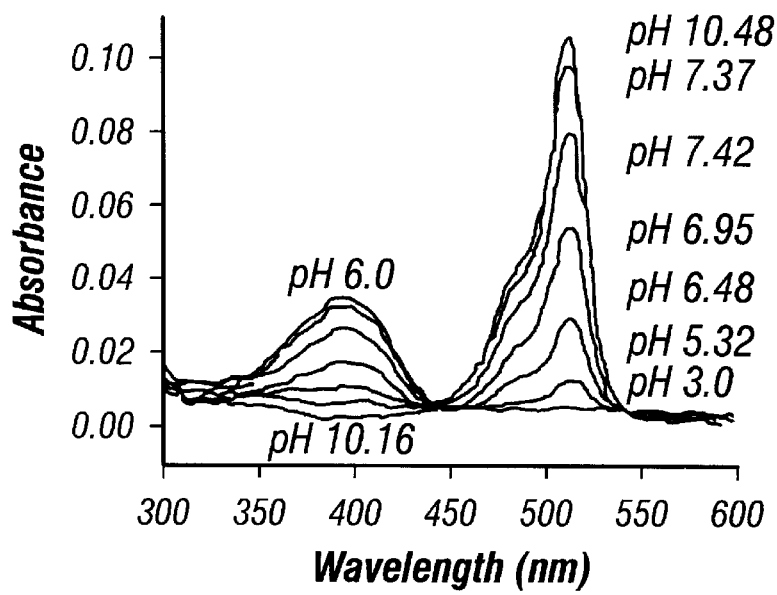
FIGS. 2A and 2B are graphs showing absorbance as a function of wavelength for the fluorescent protein pH sensor EYFP (SEQ ID NO:4; see Examples 1 and 11 for abbreviations) at various wavelengths (FIG. 2A), and the pH dependency of fluorescence of various GFP fluorescent protein sensors in vitro and in cells (FIG. 2B). The fluorescence intensity of purified recombinant GFP mutant protein (solid symbols) as a function of pH was measured in a microplate fluorometer. The fluorescence of the Golgi region of HeLa cells expressing proteins having the 81 N-terminal amino acids of the type II membrane-anchored protein galactosyltransferase (GT:UDP-galactose-β,1,4-galactosyltransferase. EC 2.4.1.22) ("GT") fused to EYFP, or EGFP, i.e., GT-EYFP or GT-EGFP (open symbols) was determined during pH titration with the ionophores monensin/nigericin in high KCL solutions.

EYFP showed an acidification-dependent decrease in the absorbance peak at 514 nm and a concomitant increase in absorbance at 390 nm (FIG. 2A). The fluorescence emission (527-nm peak) and excitation spectra decreased with decreasing pH, but the fluorescence excitation spectrum showed no compensating increase at 390 nm. Therefore, the species absorbing at 390 nm was nonfluorescent. The apparent pKa (pK'a) of EYFP was 7.1 with a Hill coefficient (n) of 1.1 (FIG. 2B).

EGFP fluorescence also was quenched with decreasing pH. The pK'a of EGFP was 6.15, and n was 0.7.

Figure 2B:
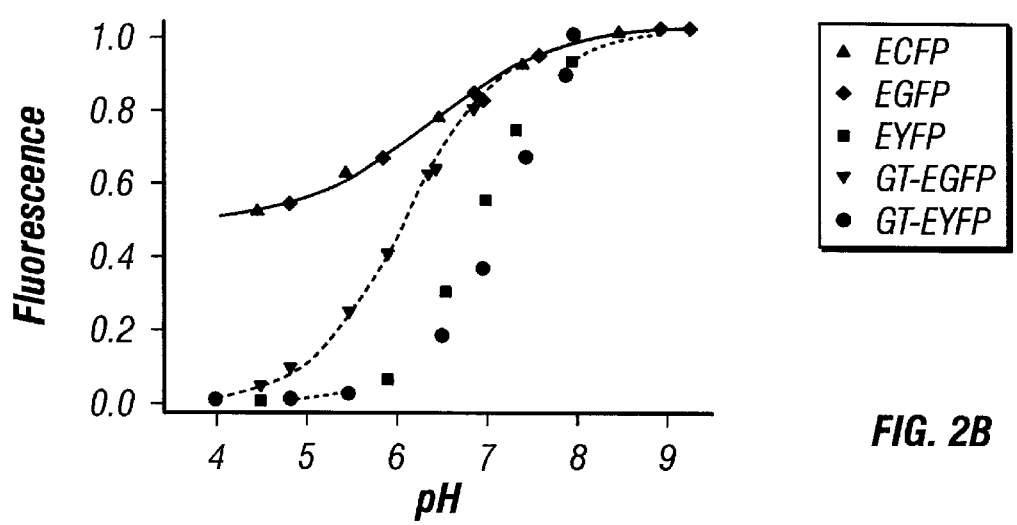

The change in fluorescence of ECFP (Tyr66→Trp in the chromophore) with pH was smaller than that of EGFP or EYFP (pK'a 6.4, n, 0.6) (FIG. 2B). The fluorescence change was reversible in the pH range 5–8.5 for all three proteins, which covers the pH range of most subcellular compartments. These results demonstrate that the GFP variants EGFP, EYFP, and ECFP can be used as fluorescent protein pH sensors.

Example 3

Measurements of pH in the Cytosol and Nucleus Using Fluorescent Protein pH Sensors HeLa cells and AT-20 cells grown on glass coverslips were transiently lipo-transfected (Lipofectin™, GIBCO) with polynucleotide constructs encoding EYFP.

Cells were imaged between 2 and 4 days after transfection at 22° C. with a cooled charge-coupled device camera (Photometrices, Tucson, Ariz.) as described in Miyawaki et al., Nature 388:882, (1997). The interference filters (Omega Optical and Chroma Technology, Brattleboro, Vt.) used for excitation and emission were 440±10 and 480±15 for ECFP; 480±15 and 535±22.5 for EGFP or EYFP. The dichroic mirrors were 455 DCLP for ECFP and 505 DCLP for EGFP or EYFP. Regions of interest were selected manually, and pixel intensities were spatially averaged after background subtraction. A binning of 2 was used to improve signal/noise and minimize photodamage and photoisomerization of EYFP. High KCl buffer plus 5 µM each of the ionophores nigericin (Fluka) and monensin (Calbiochem) was used for in situ titrations in living cells. Cells were loaded with cytosolic pH indicators by incubation with 3 µM carboxy-SNARF/AM or BCECF/AM (Molecular Probes) for 45 minutes, then washed for 30 minutes, all at 22° C.

Fluorescence of HeLa cells transfected with the gene encoding EYFP was diffusely distributed in the cytosol and nucleus. This was expected for a protein of the size of GFP (27 kDa), which is small enough to pass through nuclear pores.

The fluorescence observed with EYFP was reversible. Perfusion with $NH_4Cl$ caused an increase in fluorescence (rise in pH), which reversed upon washing out the $NH_4Cl$. Conversely, perfusion of lactate, which lowers pH, induced a decrease in fluorescence. The decrease in fluorescence was also reversible on wash-out.

Calibration of fluorescence intensity with pH in situ was accomplished with a mix of the alkali cation/H+ ionophores nigericin and monensin in bath solutions of defined pH and high K+. Fluorescence equilibrated within 1–4 minutes after each exchange of solution. These results demonstrate that EYFP, when present intracellularly, can report pH in the physiological range.

Example 4

Measurement of pH in the Mitochondrial Matrix Using Fluorescent Protein pH Sensors To measure pH in the mitochondrial matrix using mutant GFP sensor proteins, HeLa cells and neonatal rat cardiomyocytes were transfected with the fluorescent protein pH sensor EYFP-mito. A Bio-Rad MRC-1000 confocal microscope was used for analysis of the targeted protein. Microscopy analysis revealed that the transfected cells showed a fluorescence pattern indistinguishable from that of the conventional mitochondrial dye rhodamine 123.

In situ pH titration was performed with nigericin/monensin as described in Example 3. Subsequent addition of the protonophore carbonylcyanide m-chlorophenylhydrazone (CCCP) did not change the fluorescence intensity of the cells. This demonstrates that the nigericin/monensin treatment effectively collapsed the pH gradient (ΔpH)in the mitochondria.

The estimated pHm was 7.98±0.07 in HeLa cells (n=17 cells, from six experiments). Similar pH values were obtained in a HeLa cell line stably expressing EYFP-mito. Resting pH did not change by superfusion of cells with medium 10 mM glucose, which would provide cells with an oxidizable substrate, but 10 mM lactate plus 1 mM pyruvate caused an acidification, which reversed on washout. This can be accounted for by diffusion of protonated acid or by cotransport of $pyruvate^-/H^+$ through the inner mitochondrial membrane. The protonophore CCCP rapidly induced an acidification of mitochondria to about pH 7.

Example 5

Measurement of pH in the Golgi Lumen Using Fluorescent Protein pH Sensors

The type II membrane-anchored protein galactosyltransferase (GT:UDP-galactose-β,1,4-galactosyltransferase. EC 2.4.1.22) has been used as a marker of the trans cisternae of the Golgi apparatus (Roth et al., J. Cell Biol. 93:223–29, (1982)). Accordingly, polynucleotide constructs encoding portions of the GT protein fused to the mutant GFP proteins were constructed as described in Example 1 in order to use the GT sequence to target the fluorescent protein pH sensor to the endoplasmic reticulum.

The pH of the Golgi lumen was measured by transfecting HeLa or AT-20 cells with the constructs GT-ECFP, GT-EGFP, or GT-EYFP. Bright juxtanuclear fluorescence was observed, with little increase in diffuse staining above autofluorescence in most cells.

The fluorescence pattern was examined further in double-labeling experiments using rabbit polyclonal α-mannosidase II (α-manII) antibody. Double labeling fluorescence was performed as described by McCaffery et al., Methods Enzymol. 257:259–279 (1995). The α-manII antibody was prepared as described in Velasco et al., J. Cell Biol. 122:39–51 (1993). In the double-staining experiments, it was observed that labeling of the medial trans-Golgi marker α-manII overlapped with GT-EYFP fluorescence.

α-manII was also fused with ECFP, and the pattern of fluorescence obtained upon transfection of the gene was indistinguishable from that of GT-EYFP by light microcopy.

To identify the subcellular localization of GT-EYFP at higher resolution, immunogold electron microscopy was performed on ultra-thin cryosections by using antibodies against GFP. Immunogold labeling of ultra-thin sections was performed as described by McCaffery et al., supra, using rabbit polyclonal anti-GFP antibody or a monoclonal anti-TGN38 antibody.

In double-labeling experiments, GT-EYFP was found in the medial and trans Golgi, although endogenous GT is present in trans Golgi membranes. The difference in localization may occur as a result of overexpression of the GT-EYFP protein.

When protein TGN38 was used as a trans-Golgi network (TGN) marker, its immunogold localization pattern was found to overlap with that of GT-EYFP in the medial/trans-Golgi membranes. The localization data demonstrate that GT-EYFP labels the medial/trans Golgi. Thus, GT-EYFP can be used to identify the pH of this organelle.

The pH titration of GT-EYFP fluorescence in the Golgi region of the cells after treatment with nigericin/monensin was in good agreement with that of EYFP in vitro (see Example 2). Resting pH in HeLa cells was on average 6.58 (range 6.4–6.81, n=30 cells, 9 experiments). These results also demonstrate that neither fusion with GT nor the composition of the Golgi lumen affects the pH sensitivity of EYFP. Thus, Golgi-targeted EYFP can be used as a local pH indicator.

The effect of various treatments on the pH of the Golgi was next examined using Golgi-targeted EYFP.

The pH gradient across the Golgi membrane is maintained by the electrogenic ATP-dependent $H^+$ pump (V-ATPase). The V-ATPase generates a $\Delta pH$ (acidic inside) and $\Delta\psi$ (positive inside), which opposes further $H^+$ transport. The movement of counter-ions, $Cl^-$ in (or $K^+$ out), with $H^+$ uptake would shunt the $\Delta\psi$, allowing a larger $\Delta pH$ to be generated. These mechanisms were investigated in intact single HeLa cells transfected with GT-EYFP.

The macrolide antibiotic bafilomycin A1 has been shown to be a potent inhibitor of vacuolar type $H^+$ ATPases (V type). In Hela cells expressing GT-EYFP, bafilomycin A1 (0.2 $\mu M$) increased $pH_G$ by about 0.6 units, to pH 7.16 (range 7.02–7.37, n=12 cells. This suggests that the $H^+$ pump compensates for a positive H+ efflux or leak. The initial rate of Golgi alkalinization by bafilomycin A1 was 0.52 pH units per minute (range 0.3–0.77, n=12 cells), faster than that reported for other acidic compartments such as macrophage phagosomes (0.09 pH/min). Similar results regarding resting pHG and alkalinization by bafilomycin A1 were obtained when HeLa cells were transfected with GT-EGFP. Calibration of GT-EGFP in situ also mirrored its in vitro titration (FIG. 1B). Thus, both EGFP and EYFP are suitable Golgi pH indicators.

Example 6

Measuring Intracellular pH with Two Fluorescent Protein Sensors

Quantitative measurements of fluorescence with nonratiometric indicators can suffer from artifacts as a result of cell movement or focusing. To correct for these effects, the cyan-emitting mutant GT-ECFP was co-transfected into cells along with GT-EYFP. ECFP has excitation and emission peaks that can be separated from those of EYFP by appropriate filters. In addition, ECFP is less pH-sensitive than EYFP (see FIG. 2B).

Figure 3A:
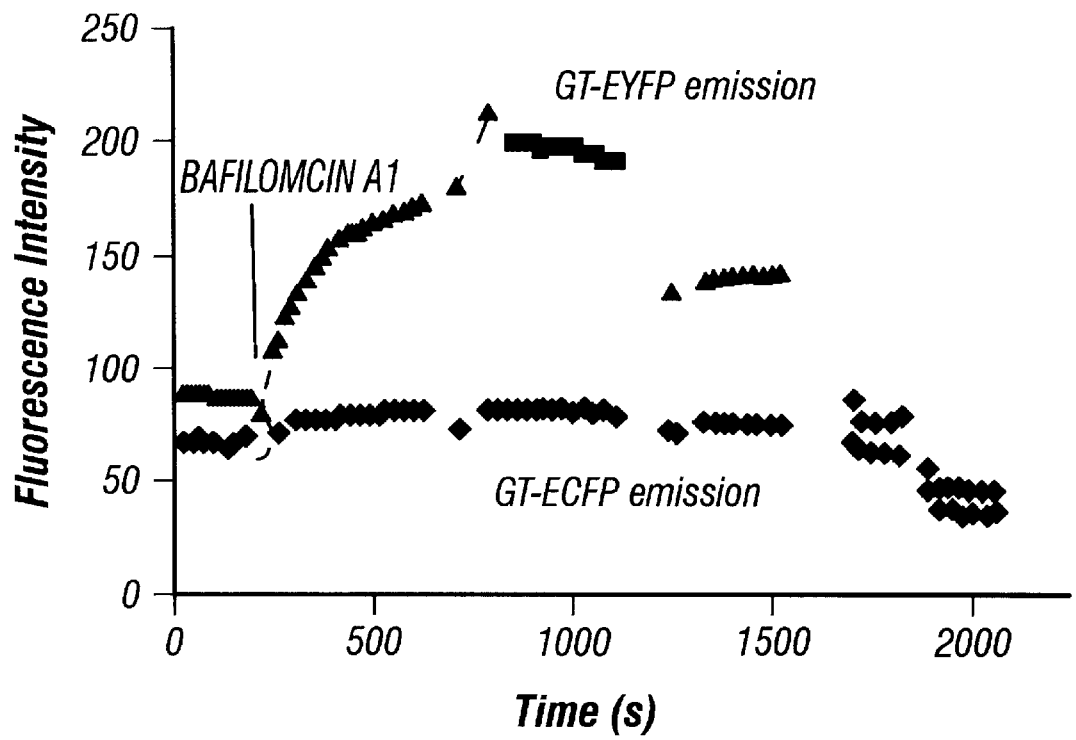
FIGS. 3A and 3B are graphs showing ratiometric measurements of $pH_G$ by cotransfecting HeLa cells with polynucleotides encoding GT-ECFP and GT-EYFP.
Figure 3B:
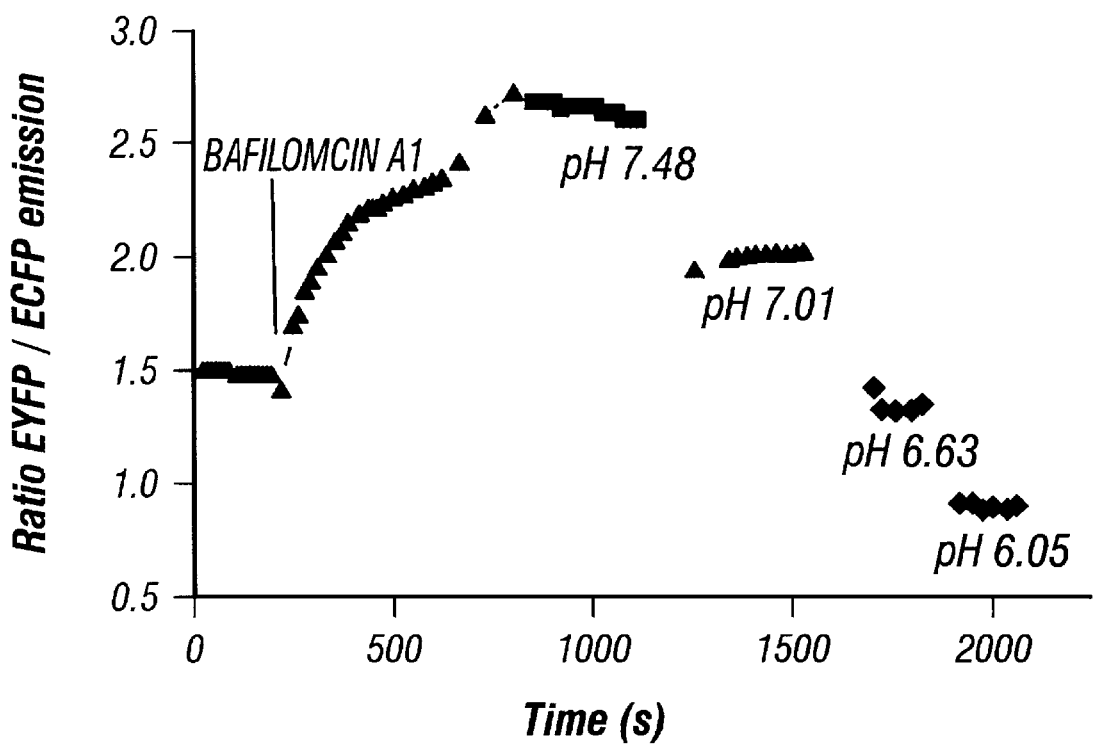

FIG. 3A demonstrates that the fluorescence of ECFP changed less than that of EYFP during the course of the experiment. Although the ratio of EYFP to ECFP emission varied between cells, probably reflecting a different concentration of GT-EYFP and GT-ECFP in the Golgi lumen, it changed with pH as expected (FIG. 3B). Bafilomcin A1 raised the GT-EYFP/GT-ECFP emission ratio, i.e, it raised $pH_G$.

Example 7

Construction of YFP THR H148G and YFP H148Q Mutants

The YFP H148G mutant was prepared using as a template a nucleic acid encoding the YFP mutation 10c, which includes the mutations S65G/V68L/S72A/Q80R/T203Y and is described in Ormö et al., Science 273:1392–95 (1997). The YFP H148G mutant was constructed using the PCR-based QUIKCHANGE™ Site-Directed Mutagenesis Kit (Stratagene, La Jolla, Calif.) following the manufacturer's instructions. The YFP H148Q mutation was similarly constructed from a nucleic acid encoding the 10C mutation.

The pKa of the YFP H148G mutant was found to be 8.0, while the YFP H148Q mutant was found to have a pKa of 7.5.

Example 8

Expression of mito-YFP H148G in the Mitochondrial Matrix at a pH Range of 7.0 to 8.4

The high pKa of the mutant YFP H148G allows it the to be used for the precise measurement of mitochondrial matrix pH both in cells at rest and in cells subject to manipulations that decrease mitochondrial pH.

This was demonstrated directly by transfecting a nucleic acid encoding mito-YFP H148G into HeLa cells using the procedures described in Example 4. YFP H148G expression was monitored by observing fluorescence over time. Mitochondrial pH was also monitored by pH titration as described in Example 3 using nigericin and monensin.

Figure 4:
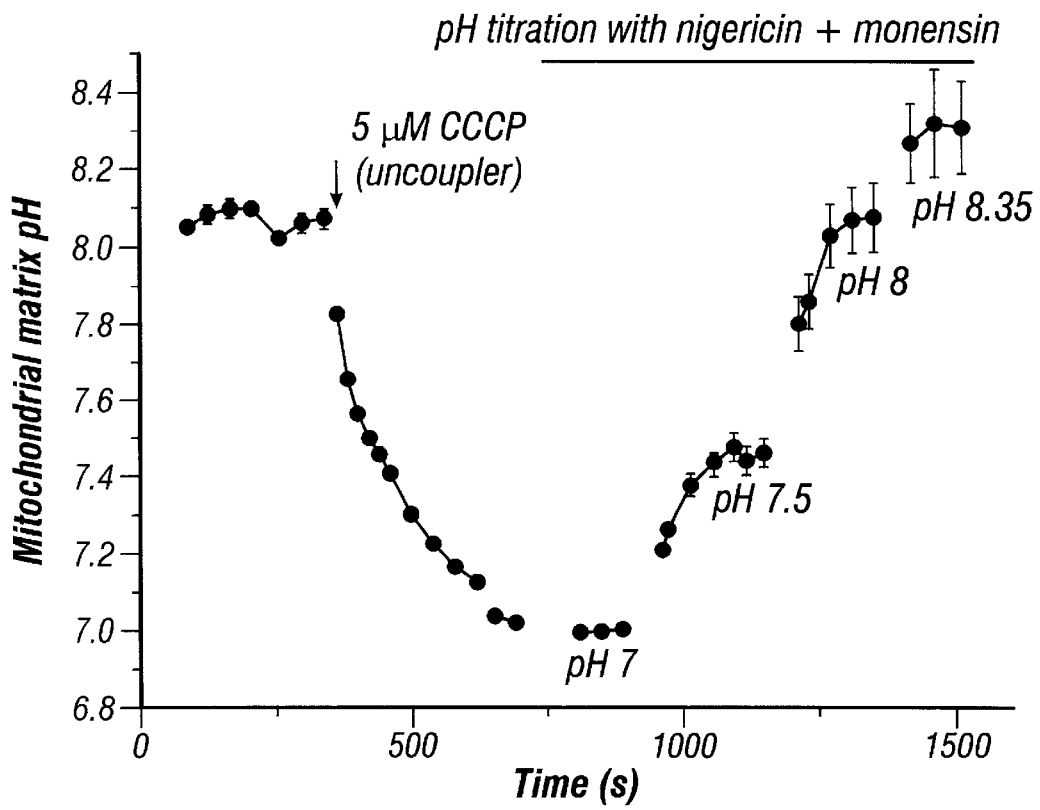
FIG. 4 is a graph showing the change in mitochondrial pH of HeLa cells expressing YFP H148G.

FIG. 4 shows that HeLa cells transfected with YFP H148G in the mitochondrial matrix were fluorescent at an initial pH of 8.0 to 8.1 (where measurements began at t≈0 seconds). 5 $\mu M$ CCCp was added at about t≈300 seconds. Although addition of 5 $\mu m$ CCCP rapidly lowered the pH to 7.0, fluorescence of mito-YFP H148G was still detectable. Then a calibration was performed by perfusing the cells with extracellular medium of ph 7, 7.5, 8, and 8.35 containing the ionophores nigericin plus monensin to equilibrate mitochondrial pH and extracellular pH. Fluorescence in mitochondria increased stepwise with each change of extracellular pH.

Figure 5:
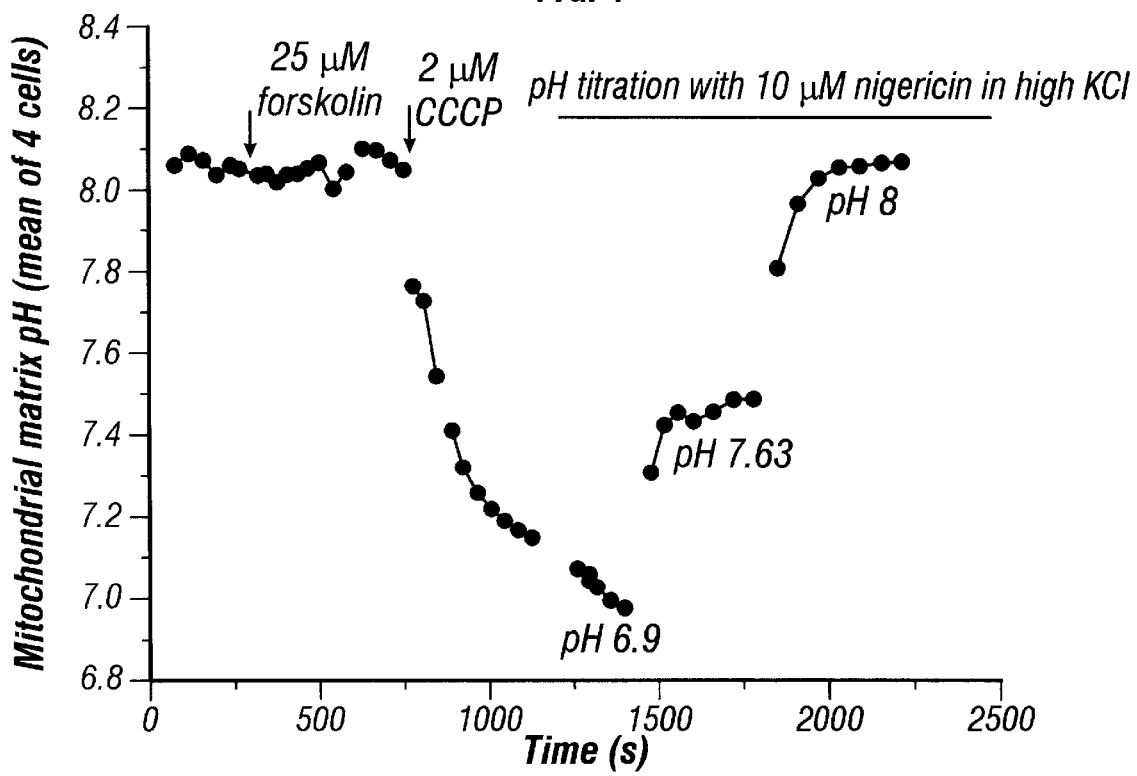
FIG. 5 is a graph showing the mitochondrial pH of chick skeletal myotubes expressing YFP H148G in the mitochondrial matrix.

Fluorescence was also examined, and pH measured, in primary cultures of chick skeletal myotubes transfected with the mito-YFP H148G mutant. FIG. 5 demonstrates that fluorescence was detectable in the mitochondrial matrix of chicken skeletal myotubes, which had a pH of 8.0–8.1 (t≈0). Fluorescence was still detectable following addition of 25 $\mu M$ forskolin, which did not affect the pH, and after addition of 2 $\mu M$ CCCP at t≈750 seconds, although CCCP caused the pH to rapidly drop to 6.9 at t≈1400 seconds. Thereafter fluorescence continued to be observed during calibration at ph 6.9, 7.6 and 8.0.

These results demonstrate mito-YFP H148G fluorescence is detectable in the mitochondrial matrix over the pH range of 7.0 to 8.4 in both established cell lines (HeLa cells) and primary cultures (chick skeletal myotubes).

Example 9

Expression of mito-YFP H148Q in Response to pH Changes

The YFP H148Q mutant has a pKa of about 7.4, which is intermediate between the pKa of EYFP and YFP mutant H148G. To demonstrate that YFP H148Q can also be used to measure mitochondrial matrix pH, a nucleic acid encoding mito-YFP-H148Q was transfected into HeLa cells. Fluorescence was measured over time (beginning at t≈0), including following the addition of 10 $\mu M$ nigericin in high KCL titration buffer at t≈500 seconds.

Figure 6:
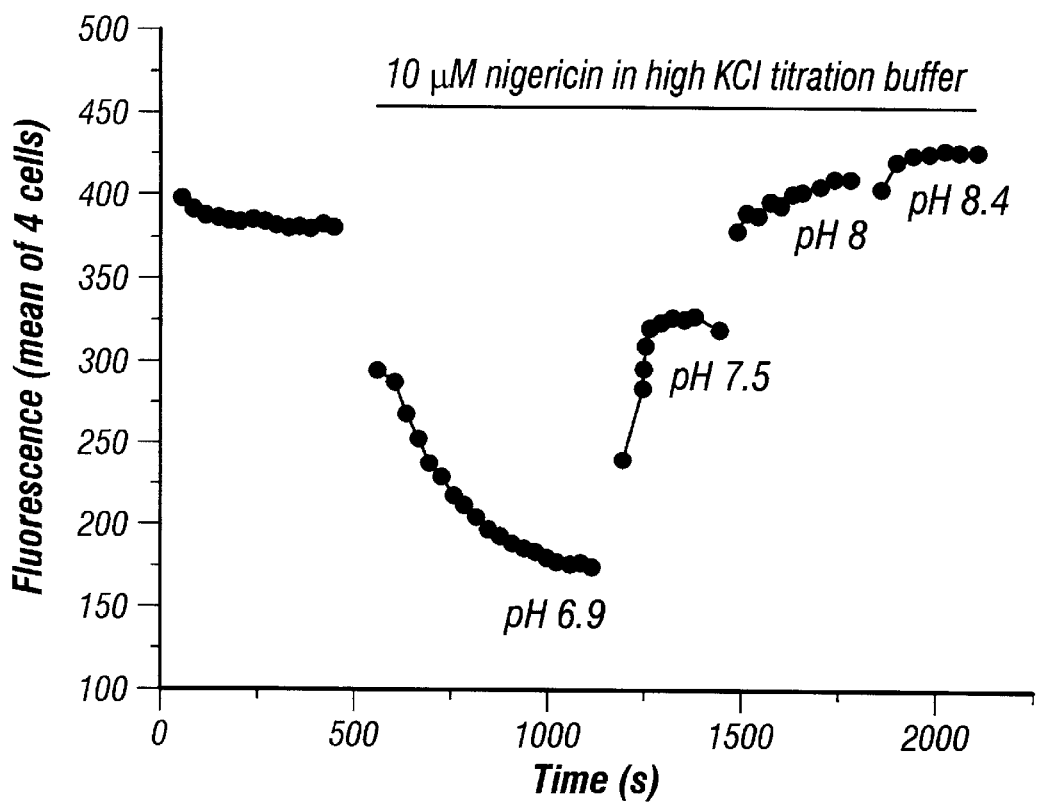
FIG. 6 is a graph showing fluorescence and pH in HeLa cells expressing YFP H148Q targeted to the mitochondrial matrix.

FIG. 6 reveals the effect of changing mitochondrial pH to 6.9, 7.5, 8, and 8.4 with the ionophore nigericin on fluorescence intensity. Fluorescence decreased to about 175 units at t≈1000 seconds by addition of nigericin, which lowered the pH to about 6.9. Fluorescence then returned stepwise to 400 units with each change of the extracellular medium. These results demonstrate that the fluorescence of the mito-YFP H148Q mutant can be used to measure the pH of the inner mitochondrial matrix.

Example 10

Measuring Intracellular pH by Coexpression of YFP H148G and a Second pH-Insensitive Sensor As is discussed above in Example 6, for quantitative measurements it is desirable to compute the fluorescence of the sensor used to measure pH with the fluorescence of a second sensor molecule whose fluorescence does not change over the pH range being tested. A ratiometric measurement is useful to correct for movement or focusing artifacts that may occur during live cell imaging experiments.

To identify a GFP sensor protein suitable for use as a reference protein for measuring mitochondrial matrix pH, the GFP mutant T203I was expressed in the mitochondria of HeLa cells. The GFP T203I mutant can be excited with light of 400 nm, which does not appreciably excite the pH sensitive YFP mutants.

Fluorescence of HeLa cells transfected with the GFP T203I mutant was monitored for about 400 seconds using an excitation ratio of 480 nm/400 nm. 10 μM CCCP was then added to the cells, and fluorescence was monitored for an additional 250 seconds. Addition of CCCP did not affect fluorescence. In control experiments, it was observed that addition of CCCP corresponded to a drop in pH of about 1 unit. Thus, the GFP T203I mutant is suitable for use as a reference, pH-insensitive mutant.

Figure 7:
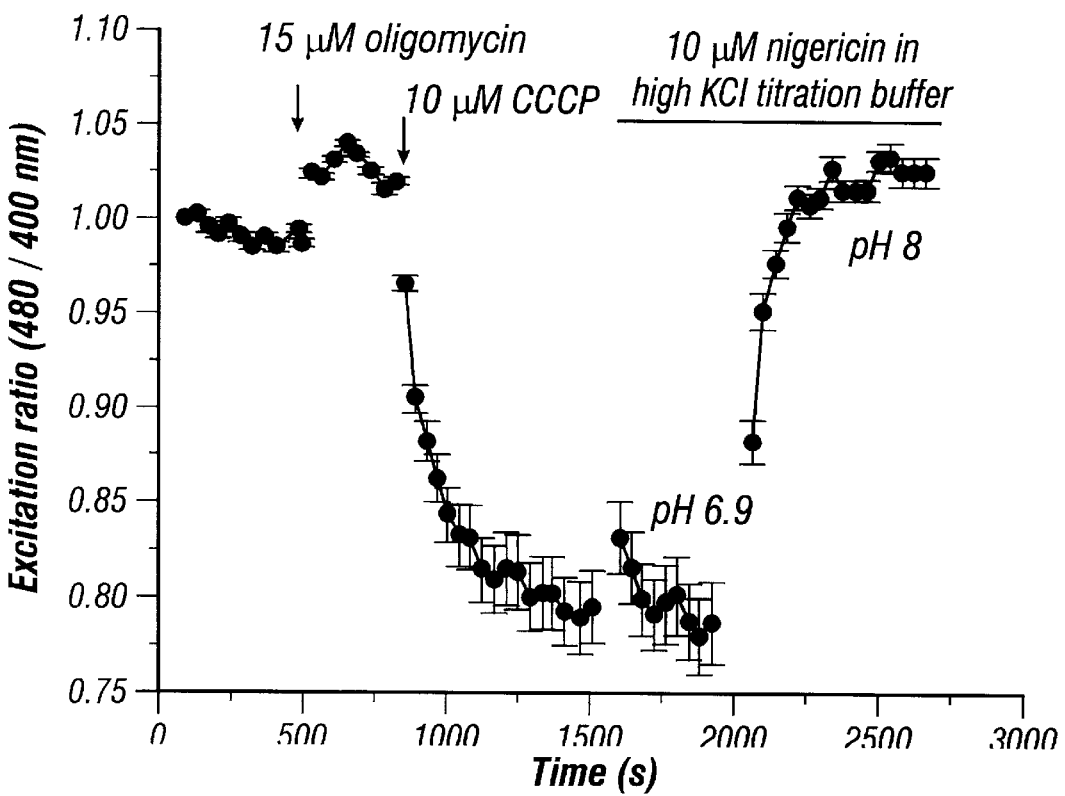
FIG. 7 is a graph showing a ratiometric measurement of mitochondrial pH following expression of YFP H148G (pH sensitive) and GFP T203I (pH insensitive) in mitochondria of HeLa cells.

HeLa cells were then transfected with the GFP T203I mutant and YFP H148G. FIG. 7 shows the change of mitochondrial pH with oligomycin and the uncoupler CCCP as the ratio of YFP H148G emission and GFP T203I emission, with excitation of 490 and 400 nm, respectively.

Example 11

Structural Characterization of YFP T203Y/S65G/V68L/S72A/H148G

The green fluorescent protein (GFP) from the jellyfish *Aequorea victoria* has been used extensively in molecular biology as a fluorescent label. The structures of WT GFP (Yang et al., Nature Biotech. 14:1246–51, 1996; Brejc et al., Proc. Natl. Acad. Sci. USA. 94:2306–11, 1997) and the variant S65T were determined in 1996 (Ormö et al., Science 273:1392–95, 1996).

Figure 8:
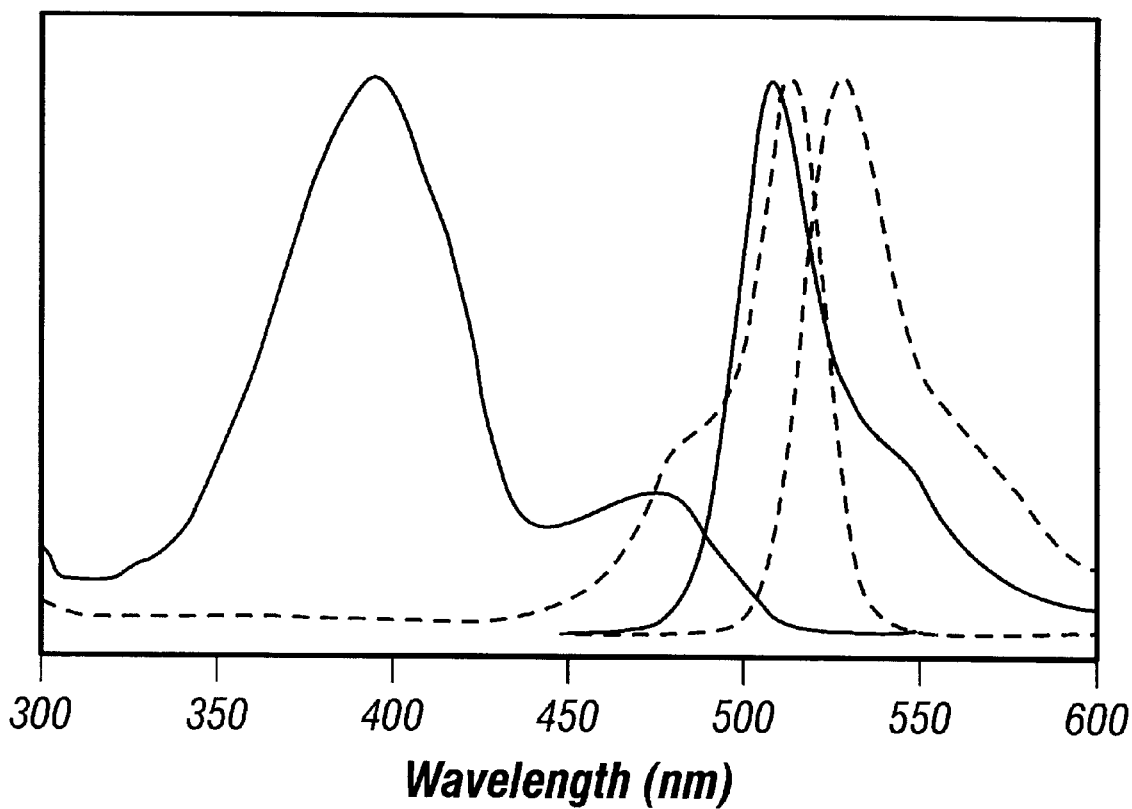
FIG. 8 is a graph showing normalized absorbance of WT GFP and YFP in 75 mM phosphate pH 8.0, 140 mM NACl. Solid lines, WT GFP; Dashed lines, YFP.

A large number of mutants have been identified that exhibit broadly varying absorption and emission maxima (Heim et al. above;, Heim et al., Curr. Biol. 6: 178–82, 1996). The yellow fluorescent protein (YFP) mutant is of particular interest since its spectrum is shifted enough to render it readily distinguishable from the spectrum of Cyan Fluorescent Protein (CFP) for FRET measurements (Tsien, Ann. Rev. Biochem. 67:509, 1998; Miawaki et al., Nature 388:882–87, 1997). WT GFP exhibits two absorption maxima, where the major band absorbs at 398 nm and the minor band at 475 nm (Morise et al., Biochemistry 13:2656–62, 1974). Excitation of either of these bands leads to emission of green light with a maximum between 504 and 508 nm (FIG. 8). Before a structure was available, GFP variants with altered spectral characteristics were identified by random mutagenesis. Some of these mutants, such as Y66H and Y66W (Tsien, Ann. Rev. Biochem. 67:509, 1998, Heim et al., Proc. Natl. Acad. Sci. (USA) 91:12501–04) result in blue-shifted absorbance and emission maxima. Others focus on changes in the immediate environment of the chromophore π system, such as S65T (Heim et al., Nature 373: 663–64, 1995) and T203I (Heim et al., Proc. Natl. Acad. Sci. (USA) 91:12501–04, 1994). At physiological pH, S65T exhibits only one major absorption band at 489 nm, red-shifted by 14 nm from WT GFP, and is almost six times brighter (Heim et al., Nature 373: 663–64, 1995). Yet, the emission spectrum is shifted by only 3 nm to 511 nm, and so cannot easily be distinguished from the wild-type emission. Random mutagenesis techniques produced only one further red-shifted variant, S65T/M153A/K238E, which increases the excitation and emission wavelengths of S65T by 15 and 3 nm respectively (Heim et al., Curr. Biol. 6: 178–82, 1996). Here is described crystal structures of the first set of GFP variants rationally designed based on the x-ray structure of GFP S65T (Ormö et al., Science 273:1392–95, 1996). These variants, termed YFPs (Yellow Fluorescent Proteins), exhibit the longest wavelength emissions of all GFPs generated by mutagenesis (FIG. 8). The YFPs fluoresce around 528 nm, red-shifted by 16 nm as compared to S65T and are easily distinguishable from S65T on a fluorescence microscope.

The specific YFP investigated is the quadruple-mutant T203Y/S65G/V68L/S72A, where the substitution T203Y was introduced based on the structural considerations detailed below and is believed responsible for the red-shift. The other three mutations have been shown to improve its brightness in live cells (Cormack et al., Gene 173:33, 1996). The T203Y mutation would have been difficult to identify by random mutagenesis since this amino acid substitution requires three substitutions at the nucleotide level. Since Thr203 is positioned close to the chromophore, it was postulated that its replacement with a tyrosine would result in π-stacking interactions between the chromophore and the highly polarizable phenol (Ormö et al., Science 273:1392–95, 1996), leading to red-shifted spectral properties. The structure of S65T suggested that an aromatic amino acid introduced in position 203 would extend into the water-filled cavity adjacent to the chromophore (Ormö et al., Science 273:1392–95, 1996). Replacement of Thr203 with any of the aromatic amino acids His, Trp,Tyr, or Phe was found to lead to the desired spectral shifts (Ormö et al., Science 273:1392–95, 1996, Dickson et al., Nature 388:355–58, 1997). The most dramatic red-shift was observed for the T203Y substitution, therefore this variant has been termed YFP.

In order to determine the role of His148 in modulating the pKa of the chromophore or its spectral properties, an additional mutation, H148G, was introduced into the YFP background. The x-ray structures of YFP and YFP H148G were analyzed in order to better correlate structural changes with spectral properties. GFP variants were prepared as described in Example 6, above. This template incorporates the mutations T203Y/S65G/V68L/S72A, as well as the ubiquitous Q80R substitution that was accidentally introduced into the gfp cDNA early on (Ormö et al., Science 273:1392–95, 1996; Chalfie et al., Science 263:802–05, 1994). All GFP variants were expressed and purified as described (Ormö et al., Science 273:1392–95, 1996).

Structural Determination of YFP H148G

YFP H148G was concentrated to 12 mg/ml in 20 mM HEPES pH 7.9. Rod-shaped crystals with approximate dimensions of 1.8×0.08×0.04 mm were grown in hanging drops containing 2 μl protein and 2 μl mother liquor at 4° C. within four days. The mother liquor contained 16% PEG 4000, 50 mM sodium acetate pH 4.6, and 50 mM ammonium acetate. X-ray diffraction data were collected from a single crystal at room temperature using a Xuong-Hamlin area detector (Hamlin, Methods. Enzymol. 114:416–52, 1985). Data were collected in space group $P2_12_12_1$ to 99% completeness at 2.6 Å resolution, and reduced using the supplied software (Howard et al., Methods Enzymol. 114:452–71, 1985). Unit cell parameters were a=52.0, b=62.7, and c=69.9. The GFP S65T coordinate file (Ormö et al., Science 273:1392–95, 1996) which served as a model for phasing was edited to reflect the mutations, with the introduced residues Tyr203 and Leu68 initially modeled as alanines to prevent model bias. A model for the anionic chromophore was obtained by semi-empirical molecular orbital calculations using AM1 in the program SPARTAN version 4.1 (Wavefunction Inc., Irvine, Calif.). The minimized structure, which was planar, compared very favorably with a related small molecule crystallographic structure (Tinant et al., Cryst. Struct. Comm. 9:671–74, 1980), and also with the model used during refinement of GFP S65T, where a simpler modeling program had been employed (Ormö et al., Science 273:1392–95, 1996).

Using the program TNT (Tronrud et al., Acta Crystallogr. Sect. A 43:489, 1987), rigid body refinement was carried out to position the isomorphous model in the unit cell of YFP H148G. Initial positional refinement was carried out using the data to 4.0 Å, then to 3.5, 3.0, and finally to 2.6 Å. Electron density maps (2Fo-Fc and Fo-Fc) were inspected using O (Tronrud et el., above), and solvent molecules were added if consistent with Fo-Fc features, and only when in proximity of hydrogen bond partners. B-factors were refined using a strong correlation between neighboring atoms due to the relatively low resolution. Since no B-factor library is available for the chromophore itself, the B-factors of all chromophore atoms were set to the values obtained in the 1.9 Å structure of GFP S65T (Ormö et al., Science 273:1392–95, 1996), and then refined as a group, with identical shifts for the grouped atoms.

Structure Determination of YFP

YFP was concentrated to 10 mg/ml in 50 mM HEPES pH 7.5. After 2 weeks crystals grew to a size of 0.03×0.12×0.8 mm at 15° C. in hanging drops containing 5≠l protein and 5≠l well solution, which contained 2.2 M sodium/potassium phosphate pH 6.9. These crystals belong to space group $P2_12_12$ and have the unit cell dimensions a=77.1, b=117.4, w and c=62.7. X-ray diffraction data were collected on two isomorphic crystals at room temperature using an Raxis-IV imaging plate mounted on a Rigaku RUH3 rotating anode generator equipped with mirrors. The data were processed with Denzo and scaled using ScalePack (Otwinowski et al., Methods Enzymol. 276:307–26, 1997). The YFP structure was solved by molecular replacement using the program AMoRe (Navaza, Acta Crystallogr. A50:157–63, 1994), with the 1.9 Å GFP S65T coordinate file as the search model (Ormö et al., Science 273:1392–95, 1996). Two solutions were identified, consistent with two molecules per asymmetric unit.

For refinement, the 2.6 Å structure of YFP H148G was chosen as the initial model, which was edited to reflect the mutations present in YFP. To avoid model bias, the occupancies of the Tyr203 side chain atoms and all chromophore atoms were set to zero during the first several rounds of refinement. Constrained NCS averaging over the A and B chains in the asymmetric unit was applied, initial refinement was carried out to 3.5 Å only, and the electron density maps (2Fo-Fc and Fo-Fc) were averaged. These maps were then inspected, and the model adjusted using O (Jones et al., Acta Crystallogr. Sect. A 47:110, 1991), followed by additional positional refinement to 2.5 Å. Chromophore and Tyr203 densities were very clear, and both were planar. The model was edited to include these groups in refinement, and solvent molecules were added where appropriate. B-factors were refined using a strong correlation between neighboring atoms due to the relatively low resolution.

Comparison of the Structure of YFP and YFP H148G

YFP crystallized in 2.2 M Na/K phosphate at pH 6.9 in spacegroup $P2_12_12$, with 2 molecules per asymmetric unit (chains A and B). The GFP S65T structure was used as a search model for molecular replacement against a 3.0 Å dataset using the program AMoRe (Navaza, Acta Crystallogr. A50:157–63, 1994), and the structure was refined. Later, the refined structure of YFP H148G (see below) was used for phasing and refinement against a 2.5 Å dataset. Even though the introduced Tyr203 and the chromophore itself were not modeled during early cycles of refinement, clear electron density for a planar chromophore and a stacked Tyr203 phenol was immediately apparent. Non-crystallographic symmetry (NCS) constraints were employed throughout refinement of the model using TNT, and maps were averaged. At the end of refinement, non-averaged maps for the A-and B-chain in the asymmetric unit were calculated and compared to each other. No obvious features were identifiable that would suggest significant differences between the two chains. A test run of refinement without any NCS constraints confirmed that the differences would be smaller than the rms error of a 2.5 Å structure. Therefore, the NCS constraints were not relaxed or eliminated. Data collection and atomic model statistics are shown in Table 33. The final R-factor of the YFP model was 19.2% for all data between 20 and 2.5 Å resolution.

TABLE 33

Data collection and atomic model statistics of YFP and YFP H148G.

|  | YFP | YFP H148G |
|---|---|---|
| Total observations | 53,039 | 29,904 |
| Unique reflections | 18,916 | 7,373 |
| Completeness[a] | 92% | 99% |
| Completeness (shell[b]) | 94% | 97% |
| Number of crystals | 2 | 1 |
| $R_{merge}$[c] (%) | 8.0% | 6.5% |
| Resolution | 2.5 Å | 2.6 Å |
| Atomic model statistics: |  |  |
| Spacegroup | $P2_12_12$ | $P2_12_12_1$ |
| Molecules per asymm. unit | 2 | 1 |
| Crystallographic R-factor | 0.192 | 0.159 |
| Protein atoms | 1,810 | 1,810 |
| Solvent atoms per asymmm. unit | 130 | 30 |
| Bond length deviations (Å) | 0.013 | 0.012 |
| Bond angle deviations (°) | 1.76 | 2.07 |
| Thermal parameter restraints (Å$^2$) | 4.53 | 3.82 |

[a]Completeness is the ratio of the number of observed I > 0 divided by the theoretically possible number of intensities.
[b]Shell is the highest resolution shell (2.56 to 2.50 Å for YFP, and 2.80 to 2.60 Å for YFP H148G)
[c]$R_{merge} = \Sigma |I_{hkl} - <I>| / \Sigma <I>$ where $<I>$ = average of individual measurements of $I_{hkl}$.

The refined YFP structure clearly shows that the overall fold is undisturbed, with an rms deviation from the GFP S65T structure of 0.36 Å for α-carbons. Three larger contact areas with adjacent molecules were identified. The largest of these covers about 722 Å2 of one monomer surface, includes a series of hydrophobic residues consisting of Ala206, Phe223, and Leu221, and also a number of hydrophilic contacts. This interface is essentially identical to the dimer interface for WT GFP described by Yang et al., Nature Biotech. 14:1246–51, 1996. High salt conditions during crystallization experiments appear to favor dimerization, as has been suggested previously (Palm et al., Nat. Struct. Biol. 4:361–65, 1997).

YFP H148G crystallized as a monomer in the presence of polyethylene glycol and acetate at pH 4.6 in spacegroup P2₁2₁2₁, isomorphous to S65T (Ormö et al., Science 273:1392–95, 1996) and the blue-emission variant BFP (Wachter et al., Biochemistry 36:9759–65, 1997). Molecular replacement using the S65T structure for phasing and refinement gave a final model with an R-factor of 15.9% for all data between 24.0 and 2.6 Å (Table 33). As with YFP, electron density for a stacked phenol was clearly visible even before the Tyr203 ring was modeled. The rms deviation between YFP H148G and S65T a-carbons is 0.31 Å, and the deviation between YFP H148G and YFP a-carbons is 0.35 Å. The b-strands of the two YFP variants overlay closely in all areas except around the $C_\alpha$ of residue 148 where a movement of 1.1 Å is observed. This movement has not been observed in other pH 4.6 structures grown under similar conditions and crystallizing in the same space group, such as the BFP structure (Wachter et al., Biochemistry 36:9759–65, 1997). Residue 148 and adjacent residues are not involved in crystal contacts, further indicating that the observed movement is due to the H148G substitution, not crystallization conditions.

π-Stacking of the introduced phenol

Figure 9:
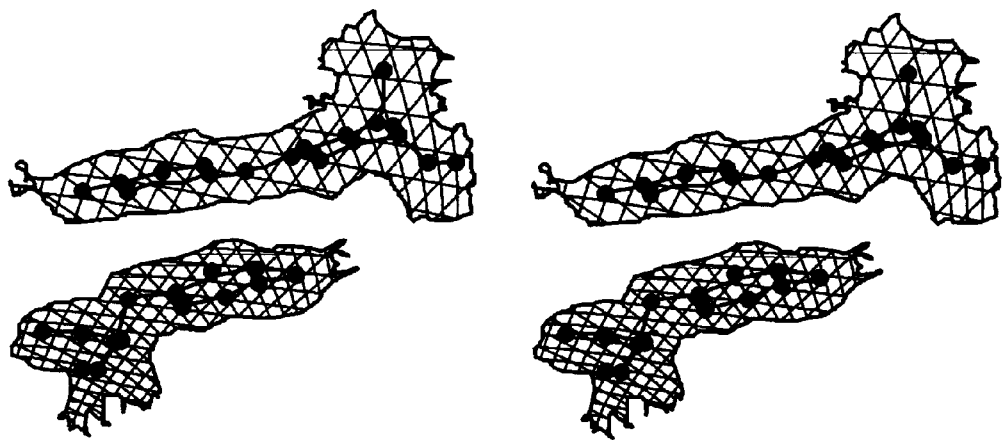
FIG. 9 is a stereoview of the $2F_o$-$F_c$ electron density map of the YFP chromophore and the stacked Tyr203 after refinement. The 2.5 Å resolution map was contoured at +1 standard deviation.

Electron densities of the chromophore and the phenol ring of Tyr203 appeared to be completely planar before the atoms for these groups were added to the model. When the tyrosine side chain was first introduced into the model, it was modelled as co-planar to the chromophore. Refinement consistently rotated the phenol ring by 12 with respect to the chromophore plane in both YFP and YFP H148G. FIG. 9 shows the electron density of the refined YFP chromophore structure together with the phenol ring of Tyr203. The distance of the closest approach between atoms of the two interacting rings is 3.3 to 3.4 Å, and occurs at that edge of the chromophore plane that is opposite the exo-methylene bond (FIG. 9). It appears that the phenol tilts towards this area of the chromophore since it is more open, with fewer atoms to clash with sterically.

The distance of largest separation between the rings is 3.5 to 3.8 Å, and occurs at the opposite edge, where steric clash with the exo-methylene carbon could occur. This range of plane-to-plane distances is typical for face-to-face π to π stacking interactions found in proteins, and consistent with interaction energy calculations that show a potential energy minimum for two horizontally stacked benzene molecules with a vertical separation of 3.3 Å (Burley et al., J. Am.Chem. Soc. 108, 7995–8001, 1986). A recent analysis of protein structures has led to the conclusion that aromatic ring interactions in an off-centered parallel orientation have an energetically favorable, stabilizing effect, and in fact are the preferred interactions (McGaughey et al., J. Biol. Chem. 273, 15458–63, 1998).

Positional shift of the chromophore

The entire chromophore ring system of YFP has moved out towards the protein surface by about 0.9 Å when compared to S65T or WT GFP. The chromophore of YFP H148G has moved in the same direction but to a lesser extent, about 0.5 Å. Overlay of all α-carbons shows that this shift is very much a local effect, only involving residues 65 to 68. The overlay suggests that this shift may be due to the compensating effects of the V68L and S65G substitutions. The Leu68 Cδ1 occupies the same space as the original Val68 Cγ1, whereas the Leu68 backbone is displaced so that the chromophore is pushed further out towards the protein surface. As part of the same movement, the Cα of Gly65 is pushed into the position of the wild-type $C_\beta$ of Ser65. The V68L and S65G substitutions had been previously found to significantly increase the brightness of GFP-expressing cells (Cormack et al., Gene 173:33, 1996) in a WT background, and were suggested to either improve folding at 37° or increase the rate of chromophore formation. It is unclear at this point why the chromophore is not shifted to the same extent in the YFP and YFP H148G structures, though both of them incorporate the V68L and SG5G mutations.

Even though the imidazolinone ring of the YFPs is not in the same position as in WT GFP (Brejc et al., Proc. Natl. Acad. Sci. USA. 94:2306–11, 1997), S65T (Ormö et al. Science 273:1392–95, 1996), and blue-fluorescent protein BFP (Wachter et al., Biochemistry 36:9759–65, 1997), no electron density consistent with partially formed or unformed chromophore is observed. This indicates that the machinery to generate the chromophore is not only intact, but more flexible than previously thought. Apparently, the exact positions of the backbone atoms of residues 65 and 67 that undergo the cyclization reaction is not as crucial as was previously suggested, based on the nearly exact superposition of the imidazolinone rings observed in WT GFP, S65T, and BFP (Yang et al., Nature Biotech. 14:1246–51, 1996; Brejc, K. et al., Proc. Natl. Acad. Sci. USA 94:2306–2311, 1997; Ormö et al., Science 273:1392–95, 1996; Palm et al., Nat. Struct. Biol. 4:361–65, 1997; Wachter et al., Biochemistry 36:9759–65, 1997).

Chromophore spectral properties, charge state and hydrogen bonding interactions

The spectral properties of the YFPs were examined. Small aliquots of protein (16 mg/ml) were diluted 48-fold into 75 mM buffer (acetate, phosphate, Tris, or CHES), 140 mM NaCl, and then scanned for absorbance between 250 and 600 nm (Shimadzu 2101 spectrophotometer at medium scan rate and room temperature). The optical density at 514 or 512 nm was plotted as a function of pH and computer-fitted to a titration curve (Kaleidagraph™, SynergySoftware).

Fluorescence measurements were carried out on a Hitachi F4500 fluorescence spectrophotometer at a constant protein concentration of approximately 0.01 mg/ml, with buffer conditions identical to those of absorbance measurements. The excitation wavelength was set to the absorbance maximum of the long-wave band of the particular mutant. The emission was scanned between 500 and 600 nm, and peak emission intensity was plotted as a function of pH and curve-fitted.

Like S65T (Kneen et al., Biophys. J. 74:1591–99, 1998), the YFPs have two absorbance maxima whose relative ratio is pH-dependent (FIG. 8 and Table 34). The UV absorption peaks at 392 (YFP) or 397 nm (YFP H148G) have been ascribed to the neutral chromophore, whereas the visible absorption peaks at 514 (YFP) or 512 nm (YFP H148G) have been ascribed to the anionic chromophore (Niwa et al., Proc. Natl. Acad. Sci. (USA) 93: 13617–22, 1996). The lower energy peak exhibits clear vibrational structure as indicated by the pronounced shoulder at 480–490 nm, and its mirror-image relationship with the emission band is striking (FIG. 8). These features are consistent with luminescence properties of large and rigid systems in condensed phases (Barltrop et al., Principles of Photochemistry, John Wiley and Sons, New York, 1978, pp. 51–52 and 78–79), and may be more pronounced in the YFPs due to decreased chromophore flexibility in the presence of the stacked phenol. Both YFPs fluoresce intensely when excited at the longer-wavelength band, with maximum emission occurring at 528 nm (FIG. 8). Fluorescence is extremely weak when the excitation occurs at the shorter-wavelength band (Table 34), even if the experiment is carried out at a pH where this peak dominates. The chromophore pKa in the intact protein was determined to be 7.00(±0.03) for YFP and 8.02 (±0.01) for YFP H148G by absorbance measurements at varying pH.

The pKa values determined by fluorescence were 6.95 (±0.03) and 7.93 (±0.04), respectively, for the two variants. The YFP pKa is remarkably similar to that of

TABLE 34

Summary of Absorption and Emission Maxima.

| | absorbance band #1 | absorbance band #2 | emission[a] band | emission[a] band |
|---|---|---|---|---|
| WT GFP | 398 | 475 | 460/508 | 504 |
| S65T | 394 | 489 | (weak) | 511 |
| YFP | 392 | 514 | (weak) | 528 |
| YEP H148G | 397 | 51122 | (weak) | 528 |

[a]The emission band #1 results from excitation at the absorbance peak #1, and the emission band #2 results from excitation at the absorbance peak #2.

EYFP(S65G/S72A/T203Y/H231L). All titration curves gave an excellent fit to a single pKa value.

It is likely that the charge state of the chromophore is mixed in the YFP crystals which were grown at pH 7, and which is the chromophore pKa. In YFP, His148 is directly hydrogen-bonded to the phenolic end of the chromophore. Its electron density is well-defined, suggesting that the imidazole ring does not change position when the chromophore ionizes. It is therefore unlikely that structural rearrangements in the immediate chromophore environment occur in response to changes in chromophore charge state. In both the YFP and YFP H148G structures, the phenolic end of the chromophore is nearly in H-bonding contact with bulk solvent via two ordered waters, and therefore may not be as tightly embedded in the protein as in WT and S65T (Brejc et al., Proc. Natl. Acad. Sci. USA. 94:2306–11, 1997, Ormö et al., Science 273:1392–95, 1996]. Structural readjustments to accommodate the anion may only affect solvent molecules.

The strong hydrogen bond to Arg96 that has been suggested to play a role in the chemistry of backbone cyclization (Ormö et al., above) is maintained in both structures. The carbonyl oxygen of the chromophore imidazolinone ring interacts with two hydrogen bond donors, Arg96 and Gln69 in YFP, and Arg96 and Gln94 in YFP H148G. This compares to similar interactions with Arg96 and Gln94 in WT and S65T. The Glu222 carboxy oxygen approaches the chromophore imidazolinone ring nitrogen to within 3.0 (YFP) and 3.3 Å (YFP H148G), considerably closer than in WT and S65T (4.3 and 4.0 Å, respectively). This close approach appears to be related to the chromophore positional shift described above. Distance and geometry for hydrogen bonding between Glu222 and the chromophore ring nitrogen are excellent in YFP, and somewhat less optimal in YFP H148G, where the presumed H-bond makes roughly a 45° angle with the chromophore plane. The YFP structure is the first GFP structure solved that suggests H-bonding interactions of the heterocyclic ring nitrogen originating from Tyr66. The most likely interpretation in terms of charge states is a deprotonated ring nitrogen and a protonated Glu222, rendering both groups neutral, however, it is clear that they share a proton.

Solvent-accessible surface and cavities

The mutation H148G was introduced into YFP to examine the effects of solvent accessibility on the fluorescent properties and the ionization constant of the chromophore. In all GFP structures examined to date, the β-barrel is somewhat perturbed around the phenolic end of the chromophore. The β-strand that covers the chromophore in that area bulges out around His148, so that the backbone from residue 144 to 150 is not directly hydrogen-bonded to the adjacent backbone between residues 165 and 170. Rather, they are laced together by forming H-bonds with the imidazole ring of His148 (Arg168 backbone N to His148 $N_{\epsilon 2}$ in S65T and WT GFP) and several water molecules. The phenolic end of the chromophore is located directly "behind" the ring of His148. It was anticipated that substitution of His with Gly would open up a solvent channel to the chromophore in the absence of other structural perturbances, or perhaps to permit the bulge to close.

The crystal structure clearly shows this anticipated solvent channel as an invagination of the protein surface with no ordered solvent molecules within. Elimination of the imidazole ring in the H148G substitution only leads to minor structural rearrangements of protein groups. The β-strands do not close up to form a directly H-bonded sheet between residues 144 and 150. Instead, the Cα of residue 148 has actually moved in the opposite direction by 1.1 Å, causing an even larger strand separation between the backbones of residues 148 and 168. The side chain of Ile167 has moved by 1.1 Å towards the space previously occupied by the imidazole ring. Nevertheless, direct solvent access to the phenolic end of the chromophore is greatly improved. Calculation of the solvent-accessible area of the chromophore using a probe sphere of radius of 1.4 Å (Connolly, Science 221:709–13, 1983), as implemented by UCSF MidasPlus|T (UCSF MidasPlus®, Computer Graphics Laboratory, University of San Francisco, Calif. 94143), shows that 22% of the chromophore surface is solvent-accessible. Only the phenolic end of the chromophore is exposed to exterior solvent, though, due to the opening in the protein wall. The phenolic oxygen of the chromophore is also hydrogen-bonded to a water molecule that is near H-bonding distance to a surface water, though a 1.4 Å probe cannot access the chromophore via this path. If both the solvent channel as well as this hydrogen bond are included, 8% of the chromophore surface is accessible to exterior solvent, entirely at the phenolic end, and 14% is accessible to interior solvent due to contact with internal cavities.

YFP H148G contains two larger interior cavities that are in contact with the chromophore cavity and filled with some ordered waters. The cavity that was largest in S65T has decreased in size from approximately 127 Å3 (S65T) to 88 Å3 (YFP H148G), because some of the space is now filled with the phenol of Tyr203. In YFP, this cavity is not accessible to a 1.4 Å probe at all since several groups have moved into this space. The more significant structural adjustments are $C_\gamma 2$ of Val224, which has moved by 1.4 Å, and $C_{\delta 1}$ of Leu42 which has moved by 2.0 Å, essentially filling the cavity. The second larger cavity in contact with the chromophore is nearly invariant for S65T, YFP, and YFP H148G, and is between 98 and 103 Å$^3$ in size.

Solvent accessibility to the chromophore

YFP H148G was found to be highly fluorescent, with bright greenish-yellow color under ordinary day light. The light-emitting properties of the fluorophore do not appear to be changed to any extent by the introduction of a solvent channel to the chromophore, indicating that significant quenching does not occur.

Since the protein fold is entirely intact in YFP H148G in spite of the generation of an opening in the β-barrel, the H148G substitution may be especially useful for allowing access of various small-molecule species to the chromophore. This substitution may be introduced into other GFP variants with a larger cavity adjacent to the chromophore, such as S65T [7] or S65G, allowing for analyte binding studies where specific spectral shifts due to the interaction with small molecules or ions of interest could be monitored. The highest ionization constant of all variants examined to date is found for the YFP H148G mutant with a pKa of 8.0. In this mutant, the chromophore is solvent exposed, consistent with a similarly high pKa when the protein is denatured (Nageswara et al., Biophys. J. 32:630–32, 1980).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A functional engineered fluorescent protein whose amino acid sequence comprises an amino acid sequence of Aequorea green fluorescent protein (SEQ ID NO: 2) containing an amino acid substitution of histidine at position 148 of SEQ ID NO: 2 for glycine or glutamine and amino acid substitutions selected from the group consisting of:
F64L/S65T/H231L of SEQ ID NO:2;
S65G/S72A/T203Y/H231 L of SEQ ID NO: 2;
S65G/V68L/Q69K/S72A/T203Y/H231 L of SEQ ID NO: 2;
K26R/F64L/S65T/Y66W/N146I/M153T/V163A/N164H/H231L of SEQ ID NO: 2; and
S65G/V68L/S72A/Q80R/T203Y of SEQ ID NO:2,
and whose emission intensity changes as pH varies between 5 and 10.

2. The functional engineered fluorescent protein of claim 1, wherein the amino acid sequence of the protein includes the substitutions S65G/S72A/T203Y/H231L in the amino acid sequence of Aequorea green fluorescent protein (SEQ ID NO: 2).

3. The functional engineered fluorescent protein of claim 1, wherein the amino acid sequence of the protein includes the substitutions S65G/V68L/Q69K/S72A/T203Y/H231L in the amino acid sequence of Aequorea green fluorescent protein (SEQ ID NO: 2).

4. The functional engineered fluorescent protein of claim 1, wherein the amino acid sequence of the protein includes the substitutions K26R/F64L/S65T/Y66W/N146I/M153T/V163A/N164H/H231L in the amino acid sequence of Aequorea green fluorescent protein (SEQ ID NO: 2).

5. The functional engineered fluorescent protein of claim 1, wherein the amino acid sequence of the protein includes the substitution H148G in the amino acid sequence of Aequorea green fluorescent protein (SEQ ID NO: 2).

6. The functional engineered fluorescent protein of claim 1, wherein the amino acid sequence of the protein includes the substitution H148Q in the amino acid sequence of Aequorea green fluorescent protein (SEQ ID NO: 2).

7. A method for determining the pH of a sample comprising:
contacting the sample with an indicator comprising a first fluorescent protein moiety whose emission intensity changes as pH varies between pH 5 and 10, wherein said first fluorescent protein moiety comprises an amino acid sequence of Aequorea green fluorescent protein (SEQ ID NO: 2) containing an amino acid substitution of histidine at position 148 of SEQ ID NO: 2 for glycine or glutamine and amino acid substitutions selected from the group consisting of:

F64L/S65T/H231L of SEQ ID NO:2;
S65G/S72A/T203Y/H231L of SEQ ID NO: 2;
S65G/V68L/Q69K/S72A/T203Y/H231L of SEQ ID NO: 2;
K26R/F64L/S65T/Y66W/N146I/M153T/V163A/N164H/H231L of SEQ ID NO:2; and
S65G/V68L/S72A/Q80R/T203Y of SEQ ID NO:2;
exciting the indicator; and
determining the intensity of light emitted by the first fluorescent protein moiety at a first wavelength, wherein the emission intensity of the first fluorescent protein moiety indicates the pH of the sample.

8. The method of claim 7, wherein the amino acid sequence of the protein includes the substitutions S65G/S72A/T203Y/H231L in the amino acid sequence of Aequorea green fluorescent protein.

9. The method of claim 7, wherein the amino acid sequence of the protein includes the substitutions S65G/V68L/Q69K/S72A/T203Y/H231L in the amino acid sequence of Aequorea green fluorescent protein (SEQ ID NO: 2).

10. The method of claim 7, wherein the amino acid sequence of the protein includes the substitutions K26R/F64L/S65T/Y66W/N146I/M153T/V163A/N164H/H231L in the amino acid sequence of Aequorea green fluorescent protein (SEQ ID NO: 2).

11. The method of claim 7, wherein the amino acid sequence of the protein includes the substitution H148G in the amino acid sequence of Aequorea green fluorescent protein (SEQ ID NO: 2).

12. The method of claim 7, wherein the amino acid sequence of the protein includes the substitution H148Q in the amino acid sequence of Aequorea green fluorescent protein (SEQ ID NO: 2).

13. The method of claim 7, wherein the sample is a biological tissue.

14. The method of claim 7, wherein the sample is a cell or a region thereof.

15. The method of claim 7, further comprising contacting the sample with a second fluorescent protein moiety whose emission intensity changes as pH varies from 5 to 10, wherein the second fluorescent protein moiety emits at a second wavelength that is distinct from the first wavelength and wherein said second fluorescent protein moiety comprises an amino acid sequence of Aequorea green fluorescent protein (SEQ ID NO:2) containing an amino acid substitution of histidine at position 148 of SEQ ID NO:2 for glycine or glutamine and amino acid substitutions selected from the group consisting of:

F64L/S65T/H231 L of SEQ ID NO:2;
S65G/S72A/T203Y/H231L of SEQ ID NO:2;
S65G/V68L/Q69K/S72A/T203Y/H231L of SEQ ID NO:2;
K26R/F64L/S65T/Y66W/N46I/M153T/V163A/N164H/H231L of SEQ ID NO:2; and S65G/V68L/S72A/Q80R/T203Y of SEQ ID NO:2;
exciting the second protein moiety;
determining the intensity of light emitted by the second protein moiety at the second wavelength; and
comparing the fluorescence at the second wavelength to the fluorescence at the first wavelength.

16. The method of claim 7, wherein the first fluorescent protein moiety is linked to a targeting sequence.

17. The method of claim 16, wherein the targeting sequence directs the first fluorescent protein moiety to a region of a cell.

18. The method of claim 17, wherein the region of the cell is the cytosol, the endoplasmic reticulum, the mitochondrial matrix, the chloroplast lumen, the medial trans-Golgi cisternae, the lumen of a lysosome, or the lumen of an endosome.

19. The method of claim 18, wherein the targeting sequence comprises the amino terminal 81 amino acids of human type II membrane-anchored protein galactosyltransferase.

20. The method of claim 18, wherein the targeting sequence comprises the amino terminal 12 amino acids of the presequence of subunit IV of cytochrome c oxidase.

21. The method of claim 20, wherein the targeting sequence further comprises the sequence Arg-Ser-Gly-Ile (SEQ ID NO: 38).

22. The method of claim 16, wherein the targeting sequence causes the first fluorescent protein moiety to be secreted from the cell.

23. The method of claim 7, wherein the first fluorescent protein moiety has a pKa greater than 6.1.

24. The method of claim 7, wherein the first fluorescent protein moiety has a pKa greater than 6.3.

25. The method of claim 7, wherein the first fluorescent protein moiety has a pKa greater than 6.9.

26. The method of claim 7, wherein the first fluorescent protein moiety has a pKa greater than 7.3.

27. The method of claim 7, wherein the first fluorescent protein moiety has a pKa greater than 7.8.

28. The method of claim 7, wherein the first fluorescent protein moiety has a pKa of 8.0.

29. A kit useful for the detection of the pH in a sample, the kit comprising carrier means containing one or more containers comprising a first container containing a functional engineered fluorescent protein whose amino acid sequence comprises an amino acid sequence of Aequorea green fluorescent protein (SEQ ID NO: 2) containing an amino acid substitution of histidine at position 148 of SEQ ID NO: 2 for glycine or glutamine and amino acid substitutions selected from the group consisting of:

F64L/S65T/H231L of SEQ ID NO:2;
S65G/S72A/T203Y/H231L of SEQ ID NO: 2;
S65G/V68L/Q69K/S72A/T203Y/H231L of SEQ ID NO: 2;
K26R/F64L/S65T/Y66W/N146I/M153T/V163A/N164H/H231L of SEQ ID NO:2; and
S65G/V68L/S72A/Q80R/T203Y of SEQ ID NO:2;
and whose emission intensity changes as pH varies between 5 and 10.

30. The functional engineered fluorescent protein of claim 2, wherein the amino acid substitution of histidine is H148G.

31. The functional engineered fluorescent protein of claim 2, wherein the amino acid sequence substitution of histidine is H148Q.

32. The functional engineered fluorescent protein of claim 5, wherein the amino acid substitutions are S65G/V68L/S72A/Q80R/T203Y of SEQ ID NO: 2.

33. The functional engineered fluorescent protein of claim 6, wherein the amino acid substitutions are S65G/V68L/S72A/Q80R/T203Y of SEQ ID NO: 2.

34. The functional engineered fluorescent protein of claim 1, further comprising a targeting sequence.

35. The method of claim 8, wherein the amino acid substitution of histidine is H148G.

36. The method of claim 8, wherein the amino acid sequence substitution of histidine is H148Q.

37. The method of claim 11, wherein the amino acid substitutions are S65G/V68L/S72A/Q80R/T203Y of SEQ ID NO: 2.

38. The method of claim 12, wherein the amino acid substitutions are S65G/V68L/S72A/Q80R/T203Y of SEQ ID NO: 2.

* * * * *

SEQUENCE LISTING

<160> NUMBER OF SEQ ID NOS: 38

<210> SEQ ID NO 1
<211> LENGTH: 716
<212> TYPE: DNA
<213> ORGANISM: Aequorea victoria
<220> FEATURE:
<221> NAME/KEY: CDS
<222> LOCATION: (1)...(714)
<223> OTHER INFORMATION: Green fluorescent protein

<400> SEQUENCE: 1

```
atg agt aaa gga gaa gaa ctt ttc act gga gtt gtc cca att ctt gtt      48
Met Ser Lys Gly Glu Glu Leu Phe Thr Gly Val Val Pro Ile Leu Val
 1               5                  10                  15 gaa tta gat ggt gat gtt aat ggg cac aaa ttt tct gtc agt gga gag      96
Glu Leu Asp Gly Asp Val Asn Gly His Lys Phe Ser Val Ser Gly Glu
             20                  25                  30 ggt gaa ggt gat gca aca tac gga aaa ctt acc ctt aaa ttt att tgc     144
Gly Glu Gly Asp Ala Thr Tyr Gly Lys Leu Thr Leu Lys Phe Ile Cys
         35                  40                  45 act act gga aaa cta cct gtt cca tgg cca aca ctt gtc act act ttc     192
Thr Thr Gly Lys Leu Pro Val Pro Trp Pro Thr Leu Val Thr Thr Phe
     50                  55                  60 tct tat ggt gtt caa tgc ttt tca aga tac cca gat cat atg aaa cgg     240
Ser Tyr Gly Val Gln Cys Phe Ser Arg Tyr Pro Asp His Met Lys Arg
 65                  70                  75                  80 cat gac ttt ttc aag agt gcc atg ccc gaa ggt tat gta cag gaa aga     288
His Asp Phe Phe Lys Ser Ala Met Pro Glu Gly Tyr Val Gln Glu Arg
                 85                  90                  95 act ata ttt ttc aaa gat gac ggg aac tac aag aca cgt gct gaa gtc     336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att     384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac     432
Asp Phe Lys Glu Asp Gly Asn Ile Leu Gly His Lys Leu Glu Tyr Asn
    130                 135                 140 tat aac tca cac aat gta tac atc atg gca gac aaa caa aag aat gga     480
Tyr Asn Ser His Asn Val Tyr Ile Met Ala Asp Lys Gln Lys Asn Gly
145                 150                 155                 160 atc aaa gtt aac ttc aaa att aga cac aac att gaa gat gga agc gtt     528
Ile Lys Val Asn Phe Lys Ile Arg His Asn Ile Glu Asp Gly Ser Val
                165                 170                 175 caa cta gca gac cat tat caa caa aat act cca att ggc gat ggc cct     576
Gln Leu Ala Asp His Tyr Gln Gln Asn Thr Pro Ile Gly Asp Gly Pro
```

```
                           180                  185                  190
gtc ctt tta cca gac aac cat tac ctg tcc aca caa tct gcc ctt tcg      624
Val Leu Leu Pro Asp Asn His Tyr Leu Ser Thr Gln Ser Ala Leu Ser
            195                  200                  205 aaa gat ccc aac gaa aag aga gac cac atg gtc ctt ctt gag ttt gta      672
Lys Asp Pro Asn Glu Lys Arg Asp His Met Val Leu Leu Glu Phe Val
    210                  215                  220 aca gct gct ggg att aca cat ggc atg gat gaa cta tac aaa              714
Thr Ala Ala Gly Ile Thr His Gly Met Asp Glu Leu Tyr Lys
225                  230                  235 ta                                                                   716

<210> SEQ ID NO 2
<211> LENGTH: 238
<212> TYPE: PRT
<213> ORGANISM: Aequorea victoria

<400> SEQUENCE: 2

Met Ser Lys Gly Glu Glu Leu Phe Thr Gly Val Val Pro Ile Leu Val
  1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 3
<211> LENGTH: 239
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: EGFP
```

-continued

```
<400> SEQUENCE: 3

Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 4
<211> LENGTH: 239
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: EYFP

<400> SEQUENCE: 4

Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Phe Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                    165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys
225                 230                 235

<210> SEQ ID NO 5
<211> LENGTH: 239
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: EYFP-V68L/Q69K

<400> SEQUENCE: 5

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                    165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
        210                 215                 220
```

```
Val Thr Ala Ala Gly Ile Thr Leu Gly Met Asp Glu Leu Tyr Lys
225                 230                 235
```

<210> SEQ ID NO 6
<211> LENGTH: 239
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: ECFP

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 7
<211> LENGTH: 238
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: YFP H148G

<400> SEQUENCE: 7

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
```

```
                35                  40                  45
Thr Thr Gly Lys Leu Pro Val Pro Trp Pro Thr Leu Val Thr Thr Phe
        50                  55                  60
Gly Tyr Gly Leu Gln Cys Phe Ala Arg Tyr Pro Asp His Met Lys Arg
 65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
               100                 105                 110
Lys Phe Glu Gly Asp Thr Leu Val Asn Arg Ile Glu Leu Lys Gly Ile
           115                 120                 125
Asp Phe Lys Glu Asp Gly Asn Ile Leu Gly His Lys Leu Glu Tyr Asn
       130                 135                 140
Tyr Asn Ser Gly Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
               165                 170                 175
Gln Leu Ala Asp His Tyr Gln Gln Asn Thr Pro Ile Gly Asp Gly Pro
           180                 185                 190
Val Leu Leu Pro Asp Asn His Tyr Leu Ser Tyr Gln Ser Ala Leu Ser
       195                 200                 205
Lys Asp Pro Asn Glu Lys Arg Asp His Met Val Leu Leu Glu Phe Val
210                 215                 220
Thr Ala Ala Gly Ile Thr His Gly Met Asp Glu Leu Tyr Lys
225                 230                 235
```

<210> SEQ ID NO 8
<211> LENGTH: 238
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: YFP H148Q

<400> SEQUENCE: 8

```
Met Ser Lys Gly Glu Glu Leu Phe Thr Gly Val Val Pro Ile Leu Val
 1               5                  10                  15
Glu Leu Asp Gly Asp Val Asn Gly His Lys Phe Ser Val Ser Gly Glu
            20                  25                  30
Gly Glu Gly Asp Ala Thr Tyr Gly Lys Leu Thr Leu Lys Phe Ile Cys
        35                  40                  45
Thr Thr Gly Lys Leu Pro Val Pro Trp Pro Thr Leu Val Thr Thr Phe
    50                  55                  60
Gly Tyr Gly Leu Gln Cys Phe Ala Arg Tyr Pro Asp His Met Lys Arg
 65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
               100                 105                 110
Lys Phe Glu Gly Asp Thr Leu Val Asn Arg Ile Glu Leu Lys Gly Ile
           115                 120                 125
Asp Phe Lys Glu Asp Gly Asn Ile Leu Gly His Lys Leu Glu Tyr Asn
       130                 135                 140
Tyr Asn Ser Gln Asn Val Tyr Ile Met Ala Asp Lys Gln Lys Asn Gly
145                 150                 155                 160
```

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
            195                 200                 205

Lys Asp Pro Asn Glu Lys Arg Asp His Met Val Leu Leu Glu Phe Val
            210                 215                 220

Thr Ala Ala Gly Ile Thr His Gly Met Asp Glu Leu Tyr Lys
225                 230                 235

<210> SEQ ID NO 9
<211> LENGTH: 239
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: EYFP-H148G

<400> SEQUENCE: 9

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser Gly Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 10
<211> LENGTH: 239
<212> TYPE: PRT
<213> ORGANISM: Aequorea victoria
<220> FEATURE:

<221> NAME/KEY: VARIANT
<222> LOCATION: (0)...(0)
<223> OTHER INFORMATION: EYFP-H148Q

<400> SEQUENCE: 10

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Phe Gly Tyr Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser Gln Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 11
<211> LENGTH: 720
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: EGFP

<400> SEQUENCE: 11

```
atggtgagca aggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggcac     420 aagctggagt acaactacaa cagccacaac gtctatatca tggccgacaa gcagaagaac     480
```

```
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720
```

```
<210> SEQ ID NO 12
<211> LENGTH: 720
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: EYFP

<400> SEQUENCE: 12
```

```
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccttcggcta cggcgtgcag tgcttcgccc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagct accagtccgc cctgagcaaa gaccccaacg agaagcgcga tcacatggtc      660
ctgctggagt tcgtgaccgc cgccgggatc actctcggca tggacgagct gtacaagtaa      720
```

```
<210> SEQ ID NO 13
<211> LENGTH: 720
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: ECFP

<400> SEQUENCE: 13
```

```
atggtgagca agggcgagga gctgttcacc ggggtggtgc ccatcctggt cgagctggac       60
ggcgacgtaa acggccacag gttcagcgtg tccggcgagg gcgagggcga tgccacctac      120
ggcaagctga ccctgaagtt catctgcacc accggcaagc tgcccgtgcc ctggcccacc      180
ctcgtgacca ccctgacctg gggcgtgcag tgcttcagcc gctaccccga ccacatgaag      240
cagcacgact tcttcaagtc cgccatgccc gaaggctacg tccaggagcg taccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacat cagccacaac gtctatatca ccgccgacaa gcagaagaac      480
ggcatcaagg cccacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720
```

<210> SEQ ID NO 14
<211> LENGTH: 720
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: EYFP-V68L/Q69K

<400> SEQUENCE: 14

```
atggtgagca aggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgaag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 15
<211> LENGTH: 714
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: YFP H148G

<400> SEQUENCE: 15

```
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tcggttatgg tcttcaatgc tttgcaagat acccagatca tatgaaacgg     240
catgactttt tcaagagtgc catgcccgaa ggttatgttc aggaaagaac tatatttttc     300
aaagatgacg ggaactacaa gacacgtgct gaagtcaagt ttgaaggtga tacccttgtt     360
aatagaatcg agttaaaagg tattgatttt aagaagatg gaaacattct tggacacaaa     420
ttggaataca actataactc aggcaatgta tacatcatgg cagacaaaca aaagaatgga     480
atcaaagtta acttcaaaat tagacacaac attgaagatg gaagcgttca actagcagac     540
cattatcaac aaaatactcc aattggcgat ggccctgtcc ttttaccaga caaccattac     600
ctgtcctatc aatctgccct ttcgaaagat cccaacgaaa agagagacca catggtcctt     660
cttgagtttg taacagctgc tgggattaca catggcatgg atgaactata caaa           714
```

<210> SEQ ID NO 16
<211> LENGTH: 714
<212> TYPE: DNA
<213> ORGANISM: Aequorea victoria
<220> FEATURE:

<221> NAME/KEY: misc_feature
<222> LOCATION: (0)...(0)
<223> OTHER INFORMATION: YFP H148Q

<400> SEQUENCE: 16

| | | | | | |
|---|---|---|---|---|---|
| atgagtaaag | gagaagaact | tttcactgga | gttgtcccaa | ttcttgttga | attagatggt | 60 |
| gatgttaatg | gcacaaaatt | ttctgtcagt | ggagagggtg | aaggtgatgc | aacatacgga | 120 |
| aaacttaccc | ttaaatttat | ttgcactact | ggaaaactac | ctgttccatg | gccaacactt | 180 |
| gtcactactt | tcggttatgg | tcttcaatgc | tttgcaagat | acccagatca | tatgaaacgg | 240 |
| catgactttt | tcaagagtgc | catgcccgaa | ggttatgttc | aggaaagaac | tatattttc | 300 |
| aaagatgacg | ggaactacaa | gacacgtgct | gaagtcaagt | ttgaaggtga | tacccttgtt | 360 |
| aatagaatcg | agttaaaagg | tattgatttt | aaagaagatg | gaaacattct | tggacacaaa | 420 |
| ttggaataca | actataactc | aggcaatgta | tacatcatgg | cagacaaaca | aaagaatgga | 480 |
| atcaaagtta | acttcaaaat | tagacacaac | attgaagatg | gaagcgttca | actagcagac | 540 |
| cattatcaac | aaaatactcc | aattggcgat | ggccctgtcc | ttttaccaga | caaccattac | 600 |
| ctgtcctatc | aatctgccct | ttcgaaagat | cccaacgaaa | agagagacca | catggtcctt | 660 |
| cttgagtttg | taacagctgc | tgggattaca | catggcatgg | atgaactata | caaa | 714 |

<210> SEQ ID NO 17
<211> LENGTH: 720
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: EYFP-H148G

<400> SEQUENCE: 17

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccttcggcta | cggcgtgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagcggcaac | gtctatatca | tggccgacaa | gcagaagaac | 480 |
| ggcatcaagg | tgaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagct | accagtccgc | cctgagcaaa | gaccccaacg | agaagcgcga | tcacatggtc | 660 |
| ctgctggagt | tcgtgaccgc | cgccgggatc | actctcggca | tggacgagct | gtacaagtaa | 720 |

<210> SEQ ID NO 18
<211> LENGTH: 720
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: EYFP-H148Q

<400> SEQUENCE: 18

| | | | | | |
|---|---|---|---|---|---|
| atggtgagca | agggcgagga | gctgttcacc | ggggtggtgc | ccatcctggt | cgagctggac | 60 |

```
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcgtgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccagaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 19
<211> LENGTH: 255
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: mito-ECFP

<400> SEQUENCE: 19

```
Met Leu Ser Leu Arg Gln Ser Ile Arg Phe Phe Lys Arg Ser Gly Ile
 1               5                  10                  15

Met Val Ser Lys Gly Glu Glu Leu Phe Thr Gly Val Val Pro Ile Leu
            20                  25                  30

Val Glu Leu Asp Gly Asp Val Asn Gly His Arg Phe Ser Val Ser Gly
        35                  40                  45

Glu Gly Glu Gly Asp Ala Thr Tyr Gly Lys Leu Thr Leu Lys Phe Ile
    50                  55                  60

Cys Thr Thr Gly Lys Leu Pro Val Pro Trp Pro Thr Leu Val Thr Thr
65                  70                  75                  80

Leu Thr Trp Gly Val Gln Cys Phe Ser Arg Tyr Pro Asp His Met Lys
                85                  90                  95

Gln His Asp Phe Phe Lys Ser Ala Met Pro Glu Gly Tyr Val Gln Glu
            100                 105                 110

Arg Thr Ile Phe Phe Lys Asp Asp Gly Asn Tyr Lys Thr Arg Ala Glu
        115                 120                 125

Val Lys Phe Glu Gly Asp Thr Leu Val Asn Arg Ile Glu Leu Lys Gly
    130                 135                 140

Ile Asp Phe Lys Glu Asp Gly Asn Ile Leu Gly His Lys Leu Glu Tyr
145                 150                 155                 160

Asn Tyr Ile Ser His Asn Val Tyr Ile Thr Ala Asp Lys Gln Lys Asn
                165                 170                 175

Gly Ile Lys Ala His Phe Lys Ile Arg His Asn Ile Glu Asp Gly Ser
            180                 185                 190

Val Gln Leu Ala Asp His Tyr Gln Gln Asn Thr Pro Ile Gly Asp Gly
        195                 200                 205

Pro Val Leu Leu Pro Asp Asn His Tyr Leu Ser Thr Gln Ser Ala Leu
    210                 215                 220

Ser Lys Asp Pro Asn Glu Lys Arg Asp His Met Val Leu Leu Glu Phe
225                 230                 235                 240
```

-continued

```
Val Thr Ala Ala Gly Ile Thr Leu Gly Met Asp Glu Leu Tyr Lys
                245                 250                 255

<210> SEQ ID NO 20
<211> LENGTH: 255
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: mito-EYFP

<400> SEQUENCE: 20

Met Leu Ser Leu Arg Gln Ser Ile Arg Phe Phe Lys Arg Ser Gly Ile
  1               5                  10                  15

Met Val Ser Lys Gly Glu Glu Leu Phe Thr Gly Val Val Pro Ile Leu
                 20                  25                  30

Val Glu Leu Asp Gly Asp Val Asn Gly His Lys Phe Ser Val Ser Gly
             35                  40                  45

Glu Gly Glu Gly Asp Ala Thr Tyr Gly Lys Leu Thr Leu Lys Phe Ile
         50                  55                  60

Cys Thr Thr Gly Lys Leu Pro Val Pro Trp Pro Thr Leu Val Thr Thr
 65                  70                  75                  80

Phe Gly Tyr Gly Val Gln Cys Phe Ala Arg Tyr Pro Asp His Met Lys
                 85                  90                  95

Gln His Asp Phe Phe Lys Ser Ala Met Pro Glu Gly Tyr Val Gln Glu
            100                 105                 110

Arg Thr Ile Phe Phe Lys Asp Asp Gly Asn Tyr Lys Thr Arg Ala Glu
        115                 120                 125

Val Lys Phe Glu Gly Asp Thr Leu Val Asn Arg Ile Glu Leu Lys Gly
    130                 135                 140

Ile Asp Phe Lys Glu Asp Gly Asn Ile Leu Gly His Lys Leu Glu Tyr
145                 150                 155                 160

Asn Tyr Asn Ser His Asn Val Tyr Ile Met Ala Asp Lys Gln Lys Asn
                165                 170                 175

Gly Ile Lys Val Asn Phe Lys Ile Arg His Asn Ile Glu Asp Gly Ser
            180                 185                 190

Val Gln Leu Ala Asp His Tyr Gln Gln Asn Thr Pro Ile Gly Asp Gly
        195                 200                 205

Pro Val Leu Leu Pro Asp Asn His Tyr Leu Ser Tyr Gln Ser Ala Leu
    210                 215                 220

Ser Lys Asp Pro Asn Glu Lys Arg Asp His Met Val Leu Leu Glu Phe
225                 230                 235                 240

Val Thr Ala Ala Gly Ile Thr Leu Gly Met Asp Glu Leu Tyr Lys
                245                 250                 255

<210> SEQ ID NO 21
<211> LENGTH: 323
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: GT-EGFP

<400> SEQUENCE: 21

Met Arg Leu Arg Glu Pro Leu Leu Ser Gly Ala Ala Met Pro Gly Ala
  1               5                  10                  15
```

-continued

```
Ser Leu Gln Arg Ala Cys Arg Leu Leu Val Ala Val Cys Ala Leu His
            20                  25                  30

Leu Gly Val Thr Leu Val Tyr Tyr Leu Ala Gly Arg Asp Leu Ser Arg
        35                  40                  45

Leu Pro Gln Leu Val Gly Val Ser Thr Pro Leu Gln Gly Gly Ser Asn
 50                  55                  60

Ser Ala Ala Ile Gly Gln Ser Gly Glu Leu Arg Thr Gly Gly
 65                  70                  75                  80

Ala Met Asp Pro Met Val Ser Lys Gly Glu Glu Leu Phe Thr Gly Val
                 85                  90                  95

Val Pro Ile Leu Val Glu Leu Asp Gly Asp Val Asn Gly His Lys Phe
            100                 105                 110

Ser Val Ser Gly Glu Gly Glu Gly Asp Ala Thr Tyr Gly Lys Leu Thr
        115                 120                 125

Leu Lys Phe Ile Cys Thr Thr Gly Lys Leu Pro Val Pro Trp Pro Thr
130                 135                 140

Leu Val Thr Thr Leu Thr Tyr Gly Val Gln Cys Phe Ser Arg Tyr Pro
145                 150                 155                 160

Asp His Met Lys Gln His Asp Phe Phe Lys Ser Ala Met Pro Glu Gly
                165                 170                 175

Tyr Val Gln Glu Arg Thr Ile Phe Phe Lys Asp Asp Gly Asn Tyr Lys
            180                 185                 190

Thr Arg Ala Glu Val Lys Phe Glu Gly Asp Thr Leu Val Asn Arg Ile
        195                 200                 205

Glu Leu Lys Gly Ile Asp Phe Lys Glu Asp Gly Asn Ile Leu Gly His
210                 215                 220

Lys Leu Glu Tyr Asn Tyr Asn Ser His Asn Val Tyr Ile Met Ala Asp
225                 230                 235                 240

Lys Gln Lys Asn Gly Ile Lys Val Asn Phe Lys Ile Arg His Asn Ile
                245                 250                 255

Glu Asp Gly Ser Val Gln Leu Ala Asp His Tyr Gln Gln Asn Thr Pro
            260                 265                 270

Ile Gly Asp Gly Pro Val Leu Leu Pro Asp Asn His Tyr Leu Ser Thr
        275                 280                 285

Gln Ser Ala Leu Ser Lys Asp Pro Asn Glu Lys Arg Asp His Met Val
290                 295                 300

Leu Leu Glu Phe Val Thr Ala Ala Gly Ile Thr Leu Gly Met Asp Glu
305                 310                 315                 320

Leu Tyr Lys
```

<210> SEQ ID NO 22
<211> LENGTH: 323
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: GT-EYFP

<400> SEQUENCE: 22

```
Met Arg Leu Arg Glu Pro Leu Leu Ser Gly Ala Ala Met Pro Gly Ala
 1               5                  10                  15

Ser Leu Gln Arg Ala Cys Arg Leu Leu Val Ala Val Cys Ala Leu His
            20                  25                  30

Leu Gly Val Thr Leu Val Tyr Tyr Leu Ala Gly Arg Asp Leu Ser Arg
        35                  40                  45
```

```
Leu Pro Gln Leu Val Gly Val Ser Thr Pro Leu Gln Gly Gly Ser Asn
 50                  55                  60

Ser Ala Ala Ile Gly Gln Ser Ser Gly Glu Leu Arg Thr Gly Gly
 65              70                  75                  80

Ala Met Asp Pro Met Val Ser Lys Gly Glu Glu Leu Phe Thr Gly Val
                 85                  90                  95

Val Pro Ile Leu Val Glu Leu Asp Gly Asp Val Asn Gly His Lys Phe
            100                 105                 110

Ser Val Ser Gly Glu Gly Glu Gly Asp Ala Thr Tyr Gly Lys Leu Thr
            115                 120                 125

Leu Lys Phe Ile Cys Thr Thr Gly Lys Leu Pro Val Pro Trp Pro Thr
            130                 135                 140

Leu Val Thr Thr Phe Gly Tyr Gly Val Gln Cys Phe Ala Arg Tyr Pro
145                 150                 155                 160

Asp His Met Lys Gln His Asp Phe Phe Lys Ser Ala Met Pro Glu Gly
                165                 170                 175

Tyr Val Gln Glu Arg Thr Ile Phe Phe Lys Asp Asp Gly Asn Tyr Lys
                180                 185                 190

Thr Arg Ala Glu Val Lys Phe Glu Gly Asp Thr Leu Val Asn Arg Ile
                195                 200                 205

Glu Leu Lys Gly Ile Asp Phe Lys Glu Asp Gly Asn Ile Leu Gly His
210                 215                 220

Lys Leu Glu Tyr Asn Tyr Asn Ser His Asn Val Tyr Ile Met Ala Asp
225                 230                 235                 240

Lys Gln Lys Asn Gly Ile Lys Val Asn Phe Lys Ile Arg His Asn Ile
                245                 250                 255

Glu Asp Gly Ser Val Gln Leu Ala Asp His Tyr Gln Gln Asn Thr Pro
                260                 265                 270

Ile Gly Asp Gly Pro Val Leu Leu Pro Asp Asn His Tyr Leu Ser Tyr
                275                 280                 285

Gln Ser Ala Leu Ser Lys Asp Pro Asn Glu Lys Arg Asp His Met Val
                290                 295                 300

Leu Leu Glu Phe Val Thr Ala Ala Gly Ile Thr Leu Gly Met Asp Glu
305                 310                 315                 320

Leu Tyr Lys

<210> SEQ ID NO 23
<211> LENGTH: 263
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: mito-YFP H148G

<400> SEQUENCE: 23

Met Leu Arg Thr Ser Ser Leu Phe Thr Arg Arg Val Gln Pro Ser Leu
 1               5                  10                  15

Phe Arg Asn Ile Leu Arg Leu Gln Ser Thr Ser Lys Gly Glu Glu Leu
                 20                  25                  30

Phe Thr Gly Val Val Pro Ile Leu Val Glu Leu Asp Gly Asp Val Asn
             35                  40                  45

Gly His Lys Phe Ser Val Ser Gly Glu Gly Glu Gly Asp Ala Thr Tyr
         50                  55                  60

Gly Lys Leu Thr Leu Lys Phe Ile Cys Thr Thr Gly Lys Leu Pro Val
```

-continued

```
                65                  70                  75                  80
        Pro Trp Pro Thr Leu Val Thr Thr Phe Gly Tyr Gly Leu Gln Cys Phe
                            85                  90                  95

Ala Arg Tyr Pro Asp His Met Lys Arg His Asp Phe Phe Lys Ser Ala
                        100                 105                 110

Met Pro Glu Gly Tyr Val Gln Glu Arg Thr Ile Phe Phe Lys Asp Asp
                        115                 120                 125

Gly Asn Tyr Lys Thr Arg Ala Glu Val Lys Phe Glu Gly Asp Thr Leu
                    130                 135                 140

Val Asn Arg Ile Glu Leu Lys Gly Ile Asp Phe Lys Glu Asp Gly Asn
        145                 150                 155                 160

Ile Leu Gly His Lys Leu Glu Tyr Asn Tyr Asn Ser Gly Asn Val Tyr
                        165                 170                 175

Ile Met Ala Asp Lys Gln Lys Asn Gly Ile Lys Val Asn Phe Lys Ile
                        180                 185                 190

Arg His Asn Ile Glu Asp Gly Ser Val Gln Leu Ala Asp His Tyr Gln
                    195                 200                 205

Gln Asn Thr Pro Ile Gly Asp Gly Pro Val Leu Leu Pro Asp Asn His
                210                 215                 220

Tyr Leu Ser Tyr Gln Ser Ala Leu Ser Lys Asp Pro Asn Glu Lys Arg
        225                 230                 235                 240

Asp His Met Val Leu Leu Glu Phe Val Thr Ala Ala Gly Ile Thr His
                        245                 250                 255

Gly Met Asp Glu Leu Tyr Lys
                    260

<210> SEQ ID NO 24
<211> LENGTH: 263
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: mito-YFP H148Q

<400> SEQUENCE: 24

Met Leu Arg Thr Ser Ser Leu Phe Thr Arg Arg Val Gln Pro Ser Leu
         1               5                  10                  15

Phe Arg Asn Ile Leu Arg Leu Gln Ser Thr Ser Lys Gly Glu Glu Leu
                        20                  25                  30

Phe Thr Gly Val Val Pro Ile Leu Val Glu Leu Asp Gly Asp Val Asn
                    35                  40                  45

Gly His Lys Phe Ser Val Ser Gly Glu Gly Glu Gly Asp Ala Thr Tyr
                50                  55                  60

Gly Lys Leu Thr Leu Lys Phe Ile Cys Thr Thr Gly Lys Leu Pro Val
        65                  70                  75                  80

Pro Trp Pro Thr Leu Val Thr Thr Phe Gly Tyr Gly Leu Gln Cys Phe
                            85                  90                  95

Ala Arg Tyr Pro Asp His Met Lys Arg His Asp Phe Phe Lys Ser Ala
                        100                 105                 110

Met Pro Glu Gly Tyr Val Gln Glu Arg Thr Ile Phe Phe Lys Asp Asp
                        115                 120                 125

Gly Asn Tyr Lys Thr Arg Ala Glu Val Lys Phe Glu Gly Asp Thr Leu
                    130                 135                 140

Val Asn Arg Ile Glu Leu Lys Gly Ile Asp Phe Lys Glu Asp Gly Asn
        145                 150                 155                 160
```

Ile Leu Gly His Lys Leu Glu Tyr Asn Tyr Asn Ser Gln Asn Val Tyr
            165                 170                 175

Ile Met Ala Asp Lys Gln Lys Asn Gly Ile Lys Val Asn Phe Lys Ile
            180                 185                 190

Arg His Asn Ile Glu Asp Gly Ser Val Gln Leu Ala Asp His Tyr Gln
            195                 200                 205

Gln Asn Thr Pro Ile Gly Asp Gly Pro Val Leu Leu Pro Asp Asn His
            210                 215                 220

Tyr Leu Ser Tyr Gln Ser Ala Leu Ser Lys Asp Pro Asn Glu Lys Arg
225                 230                 235                 240

Asp His Met Val Leu Leu Glu Phe Val Thr Ala Ala Gly Ile Thr His
            245                 250                 255

Gly Met Asp Glu Leu Tyr Lys
            260

<210> SEQ ID NO 25
<211> LENGTH: 265
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: mito-EYFP-H148G

<400> SEQUENCE: 25

Met Leu Arg Thr Ser Ser Leu Phe Thr Arg Arg Val Gln Pro Ser Leu
1               5                   10                  15

Phe Arg Asn Ile Leu Arg Leu Gln Ser Thr Met Val Ser Lys Gly Glu
            20                  25                  30

Glu Leu Phe Thr Gly Val Val Pro Ile Leu Val Glu Leu Asp Gly Asp
            35                  40                  45

Val Asn Gly His Lys Phe Ser Val Ser Gly Glu Gly Glu Gly Asp Ala
            50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Phe Gly Tyr Gly Val Gln
            85                  90                  95

Cys Phe Ala Arg Tyr Pro Asp His Met Lys Gln His Asp Phe Phe Lys
            100                 105                 110

Ser Ala Met Pro Glu Gly Tyr Val Gln Glu Arg Thr Ile Phe Phe Lys
            115                 120                 125

Asp Asp Gly Asn Tyr Lys Thr Arg Ala Glu Val Lys Phe Glu Gly Asp
            130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Tyr Asn Ser Gly Asn
            165                 170                 175

Val Tyr Ile Met Ala Asp Lys Gln Lys Asn Gly Ile Lys Val Asn Phe
            180                 185                 190

Lys Ile Arg His Asn Ile Glu Asp Gly Ser Val Gln Leu Ala Asp His
            195                 200                 205

Tyr Gln Gln Asn Thr Pro Ile Gly Asp Gly Pro Val Leu Leu Pro Asp
            210                 215                 220

Asn His Tyr Leu Ser Tyr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr Leu Gly Met Asp Glu Leu Tyr Lys
            260                 265

<210> SEQ ID NO 26
<211> LENGTH: 265
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: mito-EYFP-H148Q

<400> SEQUENCE: 26

Met Leu Arg Thr Ser Ser Leu Phe Thr Arg Arg Val Gln Pro Ser Leu
 1               5                  10                  15

Phe Arg Asn Ile Leu Arg Leu Gln Ser Thr Met Val Ser Lys Gly Glu
                20                  25                  30

Glu Leu Phe Thr Gly Val Val Pro Ile Leu Val Glu Leu Asp Gly Asp
            35                  40                  45

Val Asn Gly His Lys Phe Ser Val Ser Gly Glu Gly Glu Gly Asp Ala
        50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Phe Gly Tyr Gly Val Gln
                85                  90                  95

Cys Phe Ala Arg Tyr Pro Asp His Met Lys Gln His Asp Phe Phe Lys
                100                 105                 110

Ser Ala Met Pro Glu Gly Tyr Val Gln Glu Arg Thr Ile Phe Phe Lys
            115                 120                 125

Asp Asp Gly Asn Tyr Lys Thr Arg Ala Glu Val Lys Phe Glu Gly Asp
        130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Tyr Asn Ser Gln Asn
                165                 170                 175

Val Tyr Ile Met Ala Asp Lys Gln Lys Asn Gly Ile Lys Val Asn Phe
                180                 185                 190

Lys Ile Arg His Asn Ile Glu Asp Gly Ser Val Gln Leu Ala Asp His
            195                 200                 205

Tyr Gln Gln Asn Thr Pro Ile Gly Asp Gly Pro Val Leu Leu Pro Asp
        210                 215                 220

Asn His Tyr Leu Ser Tyr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr Leu Gly Met Asp Glu Leu Tyr Lys
            260                 265

<210> SEQ ID NO 27
<211> LENGTH: 972
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: GT-ECFP

<400> SEQUENCE: 27

```
atgaggcttc gggagccgct cctgagcggc gccgcgatgc caggcgcgtc cctacagcgg        60
gcctgccgcc tgctcgtggc cgtctgcgct ctgcaccttg gcgtcaccct cgtttactac       120
ctggctggcc gcgacctgag ccgcctgccc caactggtcg agtctccac accgctgcag        180
ggcggctcga acagtgccgc cgccatcggg cagtcctccg gggagctccg gaccggaggg       240
gccatggatc ccatggtgag caagggcgag gagctgttca ccggggtggt gcccatcctg       300
gtcgagctgg acggcgacgt aaacggccac aggttcagcg tgtccggcga gggcgagggc       360
gatgccacct acggcaagct gaccctgaag ttcatctgca ccaccggcaa gctgcccgtg       420
ccctggccca cctcgtgac cacccctgacc tggggcgtgc agtgcttcag ccgctacccc        480
gaccacatga agcagcacga cttcttcaag tccgccatgc ccgaaggcta cgtccaggag       540
cgtaccatct tcttcaagga cgacggcaac tacaagaccc gcgccgaggt gaagttcgag       600
ggcgacaccc tggtgaaccg catcgagctg aagggcatcg acttcaagga ggacggcaac       660
atcctggggc acaagctgga gtacaactac atcagccaca acgtctatat caccgccgac       720
aagcagaaga acggcatcaa ggcccacttc aagatccgcc acaacatcga ggacggcagc       780
gtgcagctcg ccgaccacta ccagcagaac acccccatcg cgacggccc cgtgctgctg        840
cccgacaacc actacctgag cacccagtcc gccctgagca agaccccaa cgagaagcgc        900
gatcacatgg tcctgctgga gttcgtgacc gccgccggga tcactctcgg catggacgag       960
ctgtacaagt aa                                                            972
```

<210> SEQ ID NO 28
<211> LENGTH: 768
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: mito-EYFP

<400> SEQUENCE: 28

```
atgctgagcc tgcgccagag catccgcttc ttcaagcgca gcggcatcat ggtgagcaag        60
ggcgaggagc tgttcaccgg ggtggtgccc atcctggtcg agctggacgg cgacgtaaac       120
ggccacaagt tcagcgtgtc cggcgagggc gagggcgatg ccacctacgg caagctgacc       180
ctgaagttca tctgcaccac cggcaagctg cccgtgccct ggcccaccct cgtgaccacc       240
ttcggctacg gcgtgcagtg cttcgcccgc taccccgacc acatgaagca gcacgacttc       300
ttcaagtccg ccatgcccga aggctacgtc caggagcgca ccatcttctt caaggacgac       360
ggcaactaca agacccgcgc cgaggtgaag ttcgagggcg acaccctggt gaaccgcatc       420
gagctgaagg gcatcgactt caaggaggac ggcaacatcc tggggcacaa gctggagtac       480
aactacaaca gccacaacgt ctatatcatg gccgacaagc agaagaacgg catcaaggtg       540
aacttcaaga tccgccacaa catcgaggac ggcagcgtgc agctcgccga ccactaccag       600
cagaacaccc ccatcggcga cggccccgtg ctgctgcccg acaaccacta cctgagctac       660
cagtccgccc tgagcaaaga ccccaacgag aagcgcgatc acatggtcct gctggagttc       720
gtgaccgccg ccgggatcac tctcggcatg gacgagctgt acaagtaa                    768
```

<210> SEQ ID NO 29
<211> LENGTH: 972
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: GT-EGFP

<400> SEQUENCE: 29

| | | | | | |
|---|---|---|---|---|---|
| atgaggcttc | gggagccgct | cctgagcggc | gccgcgatgc | caggcgcgtc | cctacagcgg | 60 |
| gcctgccgcc | tgctcgtggc | cgtctgcgct | ctgcaccttg | gcgtcaccct | cgtttactac | 120 |
| ctggctggcc | gcgacctgag | ccgcctgccc | caactggtcg | gagtctccac | accgctgcag | 180 |
| ggcggctcga | acagtgccgc | cgccatcggg | cagtcctccg | gggagctccg | gaccggaggg | 240 |
| gccatggatc | ccatggtgag | caagggcgag | gagctgttca | ccggggtggt | gcccatcctg | 300 |
| gtcgagctgg | acggcgacgt | aaacggccac | aagttcagcg | tgtccggcga | gggcgagggc | 360 |
| gatgccacct | acggcaagct | gaccctgaag | ttcatctgca | ccaccggcaa | gctgcccgtg | 420 |
| ccctggccca | ccctcgtgac | caccctgacc | tacggcgtgc | agtgcttcag | ccgctacccc | 480 |
| gaccacatga | agcagcacga | cttcttcaag | tccgccatgc | ccgaaggcta | cgtccaggag | 540 |
| cgcaccatct | tcttcaagga | cgacggcaac | tacaagaccc | gcgccgaggt | gaagttcgag | 600 |
| ggcgacaccc | tggtgaaccg | catcgagctg | aagggcatcg | acttcaagga | ggacggcaac | 660 |
| atcctggggc | acaagctgga | gtacaactac | aacagccaca | acgtctatat | catggccgac | 720 |
| aagcagaaga | acggcatcaa | ggtgaacttc | aagatccgcc | acaacatcga | ggacggcagc | 780 |
| gtgcagctcg | ccgaccacta | ccagcagaac | acccccatcg | gcgacggccc | cgtgctgctg | 840 |
| cccgacaacc | actacctgag | cacccagtcc | gccctgagca | aagacccca | cgagaagcgc | 900 |
| gatcacatgg | tcctgctgga | gttcgtgacc | gccgccggga | tcactctcgg | catggacgag | 960 |
| ctgtacaagt | aa | | | | | 972 |

<210> SEQ ID NO 30
<211> LENGTH: 972
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: GT-EYFP

<400> SEQUENCE: 30

| | | | | | |
|---|---|---|---|---|---|
| atgaggcttc | gggagccgct | cctgagcggc | gccgcgatgc | caggcgcgtc | cctacagcgg | 60 |
| gcctgccgcc | tgctcgtggc | cgtctgcgct | ctgcaccttg | gcgtcaccct | cgtttactac | 120 |
| ctggctggcc | gcgacctgag | ccgcctgccc | caactggtcg | gagtctccac | accgctgcag | 180 |
| ggcggctcga | acagtgccgc | cgccatcggg | cagtcctccg | gggagctccg | gaccggaggg | 240 |
| gccatggatc | ccatggtgag | caagggcgag | gagctgttca | ccggggtggt | gcccatcctg | 300 |
| gtcgagctgg | acggcgacgt | aaacggccac | aagttcagcg | tgtccggcga | gggcgagggc | 360 |
| gatgccacct | acggcaagct | gaccctgaag | ttcatctgca | ccaccggcaa | gctgcccgtg | 420 |
| ccctggccca | ccctcgtgac | caccttcggc | tacggcgtgc | agtgcttcgc | ccgctacccc | 480 |
| gaccacatga | agcagcacga | cttcttcaag | tccgccatgc | ccgaaggcta | cgtccaggag | 540 |
| cgcaccatct | tcttcaagga | cgacggcaac | tacaagaccc | gcgccgaggt | gaagttcgag | 600 |
| ggcgacaccc | tggtgaaccg | catcgagctg | aagggcatcg | acttcaagga | ggacggcaac | 660 |
| atcctggggc | acaagctgga | gtacaactac | aacagccaca | acgtctatat | catggccgac | 720 |
| aagcagaaga | acggcatcaa | ggtgaacttc | aagatccgcc | acaacatcga | ggacggcagc | 780 |

| | |
|---|---|
| gtgcagctcg ccgaccacta ccagcagaac accccatcg gcgacggccc cgtgctgctg | 840 |
| cccgacaacc actacctgag ctaccagtcc gccctgagca agaccccaa cgagaagcgc | 900 |
| gatcacatgg tcctgctgga gttcgtgacc gccgccggga tcactctcgg catggacgag | 960 |
| ctgtacaagt aa | 972 |

<210> SEQ ID NO 31
<211> LENGTH: 762
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: mito-YFP H148G

<400> SEQUENCE: 31

| | |
|---|---|
| atgctgagcc tgcgccagag catccgcttc ttcaagcgca gcggcatcat gagtaaagga | 60 |
| gaagaacttt tcactggagt tgtcccaatt cttgttgaat tagatggtga tgttaatggg | 120 |
| cacaaatttt ctgtcagtgg agagggtgaa ggtgatgcaa catacggaaa acttaccctt | 180 |
| aaatttattt gcactactgg aaaactacct gttccatggc caacacttgt cactactttc | 240 |
| ggttatggtc ttcaatgctt tgcaagatac ccagatcata tgaaacggca tgacttttc | 300 |
| aagagtgcca tgcccgaagg ttatgttcag gaaagaacta tattttcaa agatgacggg | 360 |
| aactacaaga cacgtgctga agtcaagttt gaaggtgata cccttgttaa tagaatcgag | 420 |
| ttaaaaggta ttgattttaa agaagatgga acattcttg gacacaaatt ggaatacaac | 480 |
| tataactcag gcaatgtata catcatggca gacaaacaaa agaatggaat caaagttaac | 540 |
| ttcaaaatta gacacaacat tgaagatgga agcgttcaac tagcagacca ttatcaacaa | 600 |
| aatactccaa ttggcgatgg ccctgtcctt ttaccagaca accattacct gtcctatcaa | 660 |
| tctgcccttt cgaaagatcc caacgaaaag agagaccaca tggtccttct tgagtttgta | 720 |
| acagctgctg ggattacaca tggcatggat gaactataca aa | 762 |

<210> SEQ ID NO 32
<211> LENGTH: 762
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: mito-YFP H148Q

<400> SEQUENCE: 32

| | |
|---|---|
| atgctgagcc tgcgccagag catccgcttc ttcaagcgca gcggcatcat gagtaaagga | 60 |
| gaagaacttt tcactggagt tgtcccaatt cttgttgaat tagatggtga tgttaatggg | 120 |
| cacaaatttt ctgtcagtgg agagggtgaa ggtgatgcaa catacggaaa acttaccctt | 180 |
| aaatttattt gcactactgg aaaactacct gttccatggc caacacttgt cactactttc | 240 |
| ggttatggtc ttcaatgctt tgcaagatac ccagatcata tgaaacggca tgacttttc | 300 |
| aagagtgcca tgcccgaagg ttatgttcag gaaagaacta tattttcaa agatgacggg | 360 |
| aactacaaga cacgtgctga agtcaagttt gaaggtgata cccttgttaa tagaatcgag | 420 |
| ttaaaaggta ttgattttaa agaagatgga acattcttg gacacaaatt ggaatacaac | 480 |
| tataactcag gcaatgtata catcatggca gacaaacaaa agaatggaat caaagttaac | 540 |
| ttcaaaatta gacacaacat tgaagatgga agcgttcaac tagcagacca ttatcaacaa | 600 |
| aatactccaa ttggcgatgg ccctgtcctt ttaccagaca accattacct gtcctatcaa | 660 |

```
tctgcccttt cgaaagatcc caacgaaaag agagaccaca tggtccttct tgagtttgta      720
acagctgctg ggattacaca tggcatggat gaactataca aa                         762

<210> SEQ ID NO 33
<211> LENGTH: 768
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: mito-EYFP-H148G

<400> SEQUENCE: 33
atgctgagcc tgcgccagag catccgcttc ttcaagcgca gcggcatcat ggtgagcaag       60
ggcgaggagc tgttcaccgg ggtggtgccc atcctggtcg agctggacgg cgacgtaaac      120
ggccacaagt tcagcgtgtc cggcgagggc gagggcgatg ccacctacgg caagctgacc      180
ctgaagttca tctgcaccac cggcaagctg cccgtgccct ggcccaccct cgtgaccacc      240
ttcggctacg gcgtgcagtg cttcgcccgc taccccgacc acatgaagca gcacgacttc      300
ttcaagtccg ccatgcccga aggctacgtc caggagcgca ccatcttctt caaggacgac      360
ggcaactaca agacccgcgc cgaggtgaag ttcgagggcg acaccctggt gaaccgcatc      420
gagctgaagg gcatcgactt caaggaggac ggcaacatcc tggggcacaa gctggagtac      480
aactacaaca gcgcaacgt ctatatcatg gccgacaagc agaagaacgg catcaaggtg       540
aacttcaaga tccgccacaa catcgaggac ggcagcgtgc agctcgccga ccactaccag      600
cagaacaccc ccatcggcga cggccccgtg ctgctgcccg acaaccacta cctgagctac      660
cagtccgccc tgagcaaaga ccccaacgag aagcgcgatc acatggtcct gctggagttc      720
gtgaccgccg ccgggatcac tctcggcatg gacgagctgt acaagtaa                  768

<210> SEQ ID NO 34
<211> LENGTH: 768
<212> TYPE: DNA
<213> ORGANISM: Aequorea victoria
<220> FEATURE:
<221> NAME/KEY: misc_feature
<222> LOCATION: (0)...(0)
<223> OTHER INFORMATION: mito-EYFP-H148Q

<400> SEQUENCE: 34
atgctgagcc tgcgccagag catccgcttc ttcaagcgca gcggcatcat ggtgagcaag       60
ggcgaggagc tgttcaccgg ggtggtgccc atcctggtcg agctggacgg cgacgtaaac      120
ggccacaagt tcagcgtgtc cggcgagggc gagggcgatg ccacctacgg caagctgacc      180
ctgaagttca tctgcaccac cggcaagctg cccgtgccct ggcccaccct cgtgaccacc      240
ttcggctacg gcgtgcagtg cttcgcccgc taccccgacc acatgaagca gcacgacttc      300
ttcaagtccg ccatgcccga aggctacgtc caggagcgca ccatcttctt caaggacgac      360
ggcaactaca agacccgcgc cgaggtgaag ttcgagggcg acaccctggt gaaccgcatc      420
gagctgaagg gcatcgactt caaggaggac ggcaacatcc tggggcacaa gctggagtac      480
aactacaaca gccagaacgt ctatatcatg gccgacaagc agaagaacgg catcaaggtg      540
aacttcaaga tccgccacaa catcgaggac ggcagcgtgc agctcgccga ccactaccag      600
cagaacaccc ccatcggcga cggccccgtg ctgctgcccg acaaccacta cctgagctac      660
cagtccgccc tgagcaaaga ccccaacgag aagcgcgatc acatggtcct gctggagttc      720
```

-continued

```
gtgaccgccg ccgggatcac tctcggcatg gacgagctgt acaagtaa          768
```

<210> SEQ ID NO 35
<211> LENGTH: 5
<212> TYPE: PRT
<213> ORGANISM: Homo sapiens

<400> SEQUENCE: 35

Lys Lys Lys Arg Lys
1               5

<210> SEQ ID NO 36
<211> LENGTH: 26
<212> TYPE: PRT
<213> ORGANISM: Homo sapiens

<400> SEQUENCE: 36

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 37
<211> LENGTH: 4
<212> TYPE: PRT
<213> ORGANISM: Homo sapiens

<400> SEQUENCE: 37

Lys Asp Glu Leu
1

<210> SEQ ID NO 38
<211> LENGTH: 4
<212> TYPE: PRT
<213> ORGANISM: Aequorea victoria
<220> FEATURE:
<221> NAME/KEY: VARIANT
<222> LOCATION: (0)...(0)
<223> OTHER INFORMATION: Linker sequence

<400> SEQUENCE: 38

Arg Ser Gly Ile